(12) United States Patent
Kirsch et al.

(10) Patent No.: US 6,723,866 B2
(45) Date of Patent: Apr. 20, 2004

(54) LIQUID-CRYSTALLINE COMPOUNDS

(75) Inventors: Peer Kirsch, Darmstadt (DE); Michael Heckmeier, Bensheim (DE); Joachim Krause, Dieburg (DE); Marc Lenges, Gross-Umstadt (DE); Gerald Unger, Weiterstadt (DE)

(73) Assignee: Merck Patent Gesellschaft mit Beschränkter Haftung, Darmstadt (DE)

( * ) Notice: Subject to any disclaimer, the term of this patent is extended or adjusted under 35 U.S.C. 154(b) by 0 days.

(21) Appl. No.: 10/202,633

(22) Filed: Jul. 25, 2002

(65) Prior Publication Data

US 2003/0216554 A1 Nov. 20, 2003

(30) Foreign Application Priority Data

Jul. 25, 2001 (DE) .......................................... 101 36 188

(51) Int. Cl.[7] ................... C07C 331/00; C07D 319/06; C07D 211/26
(52) U.S. Cl. ......................... 558/17; 549/371; 546/246
(58) Field of Search .......................... 558/17; 549/371; 546/246

(56) References Cited

U.S. PATENT DOCUMENTS 6,569,505 B2 * 5/2003 Poetsch et al. .............. 428/1.1

* cited by examiner

Primary Examiner—Deborah C Lambkin
(74) Attorney, Agent, or Firm—Millen, White, Zelano & Branigan, P.C.

(57) ABSTRACT

The invention relates to liquid-crystalline compounds of the formula I

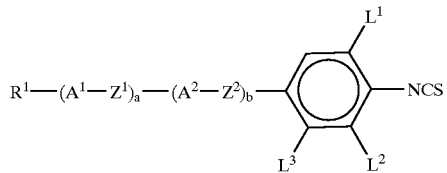

in which
$R^1$, $A^1$, $A^2$, $Z^1$, $Z^2$, a, b, $L^1$, $L^2$ and $L^3$ are as defined in claim 1, and to liquid-crystalline media comprising at least compound of the formula I and to electro-optical displays containing a liquid-crystalline medium of this type.

16 Claims, No Drawings

LIQUID-CRYSTALLINE COMPOUNDS

The present invention relates to liquid-crystalline compounds and to a liquid-crystalline medium, to the use thereof for electro-optical purposes, and to displays containing this medium.

Liquid-crystals are used principally as dielectrics in display devices, since the optical properties of such substances can be modified by an applied voltage. Electro-optical devices based on liquid crystals are extremely well known to the person skilled in the art and can be based on various effects. Examples of such devices are cells having dynamic scattering, DAP (deformation of aligned phases) cells, guest/host cells, TN cells having a twisted nematic structure, STN (supertwisted nematic) cells, SBE (super-birefringence effect) cells and OMI (optical mode interference) cells. The commonest display devices are based on the Schadt-Helfrich effect and have a twisted nematic structure.

The liquid-crystal materials must have good chemical and thermal stability and good stability to electric fields and electromagnetic radiation. Furthermore, the liquid-crystal materials should have low viscosity and produce short addressing times, low threshold voltages and high contrast in the cells.

They should furthermore have a suitable mesophase, for example a nematic or cholesteric mesophase for the above-mentioned cells, at the usual operating temperatures, i.e. in the broadest possible range above and below room temperature. Since liquid crystals are generally used as mixtures of a plurality of components, it is important that the components are readily miscible with one another. Further properties, such as the electrical conductivity, the dielectric anisotropy and the optical anisotropy, have to satisfy various requirements depending on the cell type and area of application. For example, materials for cells having a twisted nematic structure should have positive dielectric anisotropy and low electrical conductivity.

For example, for matrix liquid-crystal displays with integrated non-linear elements for switching individual pixels (MLC displays), media having large positive dielectric anisotropy, broad nematic phases, relatively low birefringence, very high specific resistance, good UV and temperature stability and low vapour pressure are desired.

Matrix liquid-crystal displays of this type are known. Non-linear elements which can be used for individual switching of the individual pixels are, for example, active elements (i.e. transistors). The term "active matrix" is then used, where a distinction can be made between two types:
1. MOS (metal oxide semiconductor) or other diodes on a silicon wafer as substrate.
2. Thin-film transistors (TFTs) on a glass plate as substrate.

The use of single-crystal silicon as substrate material restricts the display size, since even modular assembly of various part-displays results in problems at the joins.

In the case of the more promising type 2, which is preferred, the electro-optical effect used is usually the TN effect. A distinction is made between two technologies: TFTs comprising compound semiconductors, such as, for example, CdSe, or TFTs based on polycrystalline or amorphous silicon. Intensive work is being carried out worldwide on the latter technology.

The TFT matrix is applied to the inside of one glass plate of the display, while the other glass plate carries the transparent counterelectrode on its inside. Compared with the size of the pixel electrode, the TFT is very small and has virtually no adverse effect on the image. This technology can also be extended to fully color-capable displays, in which a mosaic of red, green and blue filters is arranged in such a way that a filter element is opposite each switchable pixel.

The TFT displays usually operate as TN cells with crossed polarisers in transmission and are illuminated from the back.

The term MLC displays here covers any matrix display with integrated non-linear elements, i.e., besides the active matrix, also displays with passive elements, such as varistors or diodes (MIM=metal-insulator-metal).

MLC displays of this type are particularly suitable for TV applications (for example pocket TVs) or for high-information displays for computer applications (laptops) and in automobile or aircraft construction. Besides problems regarding the angle dependence of the contrast and the response times, difficulties also arise in MLC displays due to insufficiently high specific resistance of the liquid-crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, Sept. 1984: A 210–288 Matrix LCD Controlled by Double Stage Diode Rings, p. 141 ff, Paris; STROMER, M., Proc. Eurodisplay 84, Sept. 1984: Design of Thin Film Transistors for Matrix Addressing of Television Liquid Crystal Displays, p. 145 ff, Paris]. With decreasing resistance, the contrast of an MLC display deteriorates, and the problem of after-image elimination may occur. Since the specific resistance of the liquid-crystal mixture generally drops over the life of an MLC display owing to interaction with the interior surfaces of the display, a high (initial) resistance is very important in order to obtain acceptable service lives. In particular in the case of low-volt mixtures, it was hitherto impossible to achieve very high specific resistance values. It is furthermore important that the specific resistance exhibits the smallest possible increase with increasing temperature and after heating and/or UV exposure. The low-temperature properties of the mixtures from the prior art are also particularly disadvantageous. It is demanded that no crystallisation and/or smectic phases occur, even at low temperatures, and the temperature dependence of the viscosity is as low as possible. The MLC displays from the prior art thus do not meet today's requirements.

There thus continues to be a great demand for MLC displays having very high specific resistance at the same time as a large working-temperature range, short response times even at low temperatures and low threshold voltage which do not have these disadvantages, or only do so to a reduced extent.

In TN (Schadt-Helfrich) cells, media are desired which facilitate the following advantages in the cells:
  extended nematic phase range (in particular down to low temperatures)
  the ability to switch at extremely low temperatures (outdoor use, automobile, avionics)
  increased resistance to UV radiation (longer service life)
  high $\Delta n$ for faster response times The media available from the prior art do not allow these advantages to be achieved while simultaneously retaining the other parameters.

In the case of supertwisted (STN) cells, media are desired which enable greater multiplexability and/or lower threshold voltages and/or broader nematic phase ranges (in particular at low temperatures). To this end, a further widening of the available parameter latitude (clearing point, smectic-nematic transition or melting point, viscosity, dielectric parameters, elastic parameters) is urgently desired.

The invention has an object of providing media, in particular for MLC, IPS, TN or STN displays of this type, which do not have the above-mentioned disadvantages or only do so to a reduced extent, and preferably simultaneously have very high specific resistances and low threshold voltages. This object requires liquid-crystalline compounds which have a high clearing point and low rotational viscosity.

Upon further study of the specification and appended claims, further objects and advantages of this invention will become apparent to those skilled in the art.

It has now been found that among others, these, objects can be achieved if the liquid-crystalline compounds according to the invention are used.

The invention thus relates to liquid-crystalline compounds of the formula I

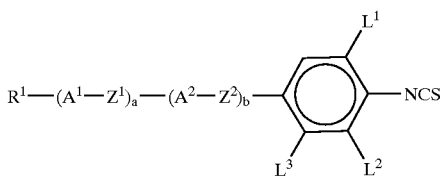

in which
$R^1$ is an alkyl radical having from 1 to 15 carbon atoms which is unsubstituted, monosubstituted by CN or $CF_3$ or at least monosubstituted by halogen, where, in addition, one or more $CH_2$ groups in these radicals may be replaced by —O—, —S—, —CH=CH—, —C≡C—, —OC—O— or —O—CO— in such a way that O atoms are not linked directly to one another,
$A^1$ and $A^2$ are each, independently of one another,
  a) a 1,4-cyclohexenylene or 1,4-cyclohexylene radical, in which one or two non-adjacent $CH_2$ groups may be replaced by —O— or —S—,
  b) a 1,4-phenylene radical, in which one or two CH groups may be replaced by N,
  c) a radical from the group consisting of piperidine-1,4-diyl, 1,4-bicyclo[2.2.2]octylene, phenanthrene-2,7-diyl, naphthalene-2,6-diyl, decahydronaphthalene-2,6-diyl and 1,2,3,4-tetrahydronaphthalene-2,6-diyl,
  where the radicals a), b) and c) may be monosubstituted or polysubstituted by halogen atoms,
$Z^1$ and $Z^2$ are each, independently of one another, —CO—O—, —O—CO—, —$CF_2$O—, —O$CF_2$—, —$CH_2$O—, —O$CH_2$—, —$CH_2CH_2$—, —($CH_2$)$_4$—, —$C_2F_4$—, —$CH_2CF_2$—, —$CF_2CH_2$—, —CF=CF—, —CH=CH—, —C≡C— or a single bond, with the proviso that at least one of the bridges $Z^1$ and $Z^2$ is —$CF_2$O— or —O$CF_2$—,
a is 0, 1 or 2,
b is 1 or 2, and
$L^1$, $L^2$ and $L^3$ are each, independently of one another, H, F or Cl.

The invention furthermore relates to the use of the compounds of the formula I in liquid-crystalline media.

The compounds of the formula I have a broad range of applications. Depending on the choice of substituents, these compounds can serve as base materials of which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or in order to optimise its threshold voltage and/or its viscosity.

In the pure state, the compounds of the formula I are colorless and form liquid-crystalline mesophases in a temperature range which is favorably located for electro-optical use. In particular, the compounds according to the invention are distinguished by their high clearing point, their broad nematic phase range, their high dielectric anisotropy and their low rotational viscosity values. They are stable chemically, thermally and to light.

The invention relates in particular to the compounds of the formula I in which $R^1$ is alkyl having from 1 to 10 carbon atoms or an alkenyl radical having from 2 to 10 carbon atoms.

Particular preference is given to compounds of the formula I in which a=b=1 or a=b=2. $Z^1$ and $Z^2$ are preferably a single bond, furthermore —$CF_2$O—, —O$CF_2$—, —$C_2F_4$—, —$CH_2$O—, —O$CH_2$— or —COO—, a is preferably 0.

If $R^1$ is an alkyl radical and/or an alkoxy radical, this may be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexyloxy or heptyloxy, furthermore methyl, octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6-, or 7-oxaoctyl, 2-, 3-, 4-, 5-, 6-, 7- or 8-oxanonyl, or 2-, 3-, 4-, 5-, 6-, 7-, 8-, or 9-oxadecyl.

If $R^1$ is an alkenyl radical, this may be straight-chain or branched. It is preferably straight-chain and has from 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, 4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If $R^1$ is an alkyl radical in which one $CH_2$ group has been replaced by —O— and one has been replaced by —CO—, these are preferably adjacent. These thus contain an acyloxy group —CO—O— or an oxycarbonyl group —O—CO. These are preferably straight-chain and have from 2 to 6 carbon atoms.

Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)-propyl, 3-(ethoxycarbonyl)propyl or 4-(methoxycarbonyl)butyl.

If $R^1$ is an alkyl or alkenyl radical which is monosubstituted by CN or $CF_3$, this radical is preferably straight-chain. The substitution by CN or $CF_3$ is in any desired position.

If $R^1$ is an alkyl or alkenyl radical which is at least monosubstituted by halogen, this radical is preferably straight-chain, and halogen is preferably F or Cl. In the case of polysubstitution, halogen is preferably F. The resultant radicals also include perfluorinated radicals. In the case of monosubstitution, the fluorine or chlorine substituent may be in any desired position, but is preferably in the ω-position.

Compounds of the formula I containing branched wing groups $R^1$ may occasionally be of importance owing to better solubility in the conventional liquid-crystalline base materials, but in particular as chiral dopants if they are optically active. Smectic compounds of this type are suitable as components of ferroelectric materials.

Compounds of the formula I having $S_A$ phases are suitable for thermally addressed displays.

Branched groups of this type generally contain not more than one chain branch. Preferred branched radicals $R^1$ and/or $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexyloxy, 1-methylhexyloxy and 1-methylheptyloxy.

For reasons of simplicity, Cyc below denotes a 1,4-cyclohexylene radical, Che denotes a 1,4-cyclohexenylene radical, Dio denotes a 1,3-dioxane-2,5-diyl radical, Dit denotes a 1,3-dithiane-2,5-diyl radical, Phe denotes a 1,4-phenylene radical, Pyd denotes a pyridine-2,5-diyl radical, Pyr denotes a pyrimidine-2,5-diyl radical, Bi denotes a bicyclo[2.2.2]octylene radical, PheF denotes a 2- or 3-fluoro-1,4-phenylene radical, PheFF denotes a 2,3-difluoro- or 2,6-difluoro-1,4-phenylene radical, Nap denotes a substituted or unsubstituted naphthalene radical, Dec denotes a decahydronaphthalene radical, and Phen denotes a substituted or unsubstituted phenanthrene radical.

For reasons of simplicity, $A^3$-NCS below denotes

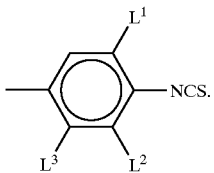

The compounds of the formula I accordingly include the preferred bicyclic compounds of the sub-formulae Ia to Ij:

| | |
|---|---|
| $R^1$-Cyc-$Z^2$-$A^3$-NCS | Ia |
| $R^1$-Phe-$Z^2$-$A^3$-NCS | Ib |
| $R^1$-Pyr-$Z^2$-$A^3$-NCS | Ic |
| $R^1$-Dio-$Z^2$-$A^3$-NCS | Id |
| $R^1$-Bi-$Z^2$-$A^3$-NCS | Ie |
| $R^1$-PheF-$Z^2$-$A^3$-NCS | If |
| $R^1$-PheFF-$Z^2$-$A^3$-NCS | Ig |
| $R^1$-Nap-$Z^2$-$A^3$-NCS | Ih |
| $R^1$-Dec-$Z^2$-$A^3$-NCS | Ii |
| $R^1$-Phen-$Z^2$-$A^3$-NCS | Ij |

The compounds of the formula I accordingly include the preferred tricyclic compounds of the sub-formulae ik to iv:

| | |
|---|---|
| $R^1$-Cyc-$Z^1$-Cyc-$Z^2$-$A^3$-NCS | Ik |
| $R^1$-Cyc-$Z^1$-Phe-$Z^2$-$A^3$-NCS | Il |
| $R^1$-Cyc-$Z^1$-PheF-$Z^2$-$A^3$-NCS | Im |
| $R^1$-Cyc-$Z^1$-PheFF-$Z^2$-$A^3$-NCS | In |
| $R^1$-Phe-$Z^1$-Phe-$Z^2$-$A^3$-NCS | Io |
| $R^1$-Cyc-$Z^1$-Dio-$Z^2$-$A^3$-NCS | Ip |
| $R^1$-Dio-$Z^1$-Cyc-$Z^2$-$A^3$-NCS | Iq |
| $R^1$-Dec-$Z^1$-Cyc-$Z^2$-$A^3$-NCS | Ir |
| $R^1$-Phe-$Z^1$-PheF-$Z^2$-$A^3$-NCS | Is |

-continued

| | |
|---|---|
| $R^1$-Phe-$Z^1$-PheFF-$Z^2$-$A^3$-NCS | It |
| $R^1$-Pyr-$Z^1$-Phe-$Z^2$-$A^3$-NCS | Iu |
| $R^1$-Phe-$Z^1$-Phen-$Z^2$-$A^3$-NCS | Iv |

Of these, particular preference is given to the compounds of the sub-formulae Ia, Ib, Id, Ik, and Il.

$R^1$ in the formula I and in all sub-formulae is preferably straight-chain unsubstituted alkyl, alkoxy, alkenyloxy or alkenyl having 1 to 10 carbon atoms.

$A^2$ is preferably Phe, PheF, PheFF, Cyc or Che, furthermore Pyr or Dio, Dec or Nap. The compounds of the formula I preferably contain not more than one of the radicals Bi, Pyd, Pyr, Dio, Dit, Nap or Dec.

Preference is also given to all compounds of the formula I and of all sub-formulae in which $A^1$ is a monosubstituted or disubstituted 1,4-phenylene. These are, in particular, 2-fluoro-1,4-phenylene, 3-fluoro-1,4-phenylene, 2,3-difluoro-1,4-phenylene and 2,6-difluoro-1,4-phenylene.

Preferred smaller groups of compounds of the formula I are those of the sub-formulae I1 to I94:

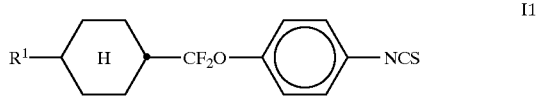

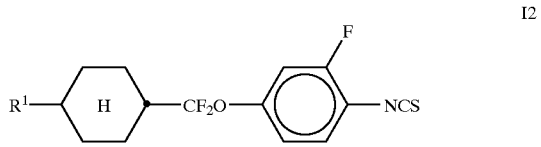

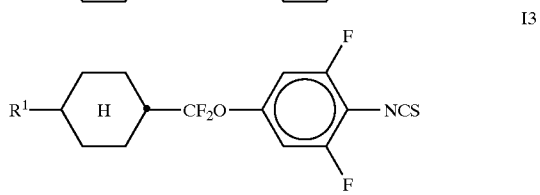

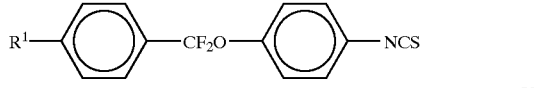

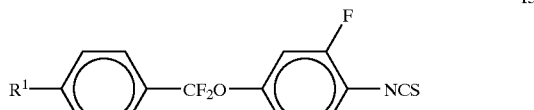

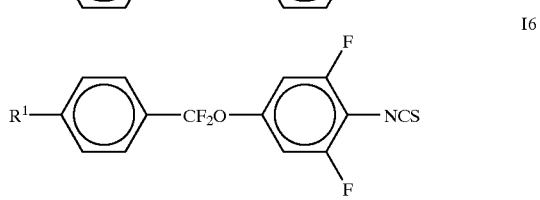

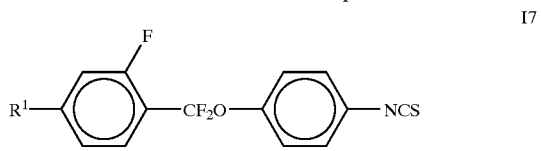

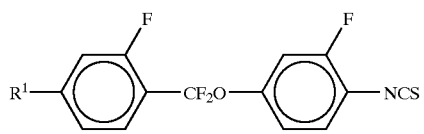
I8
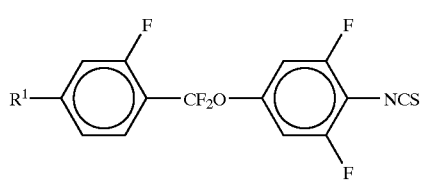
I9
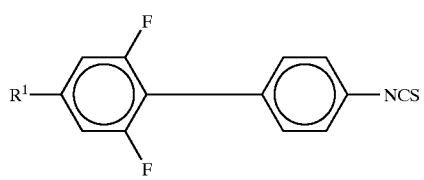
I10
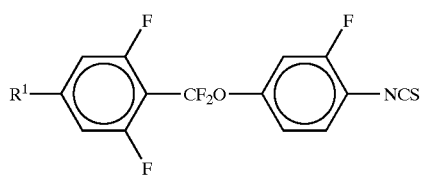
I11
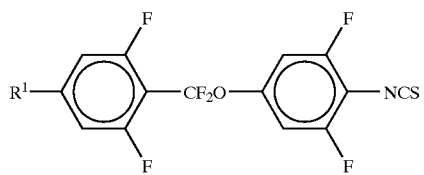
I12
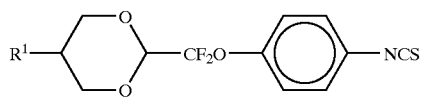
I13
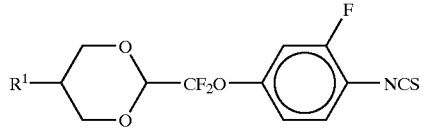
I14
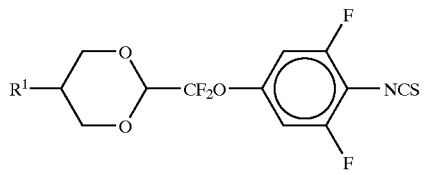
I15
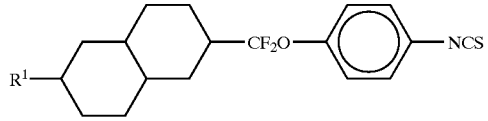
I16
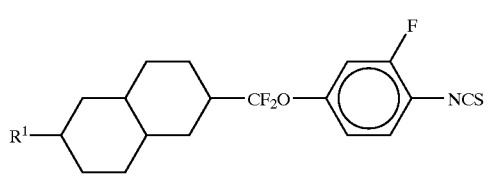
I17
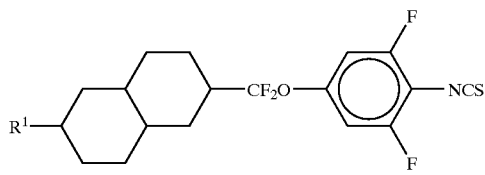
I18
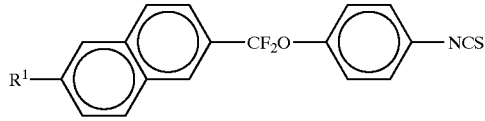
I19
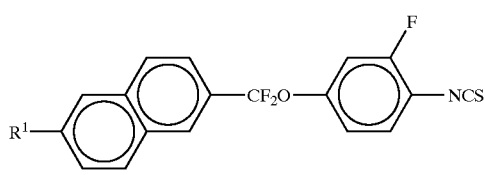
I20
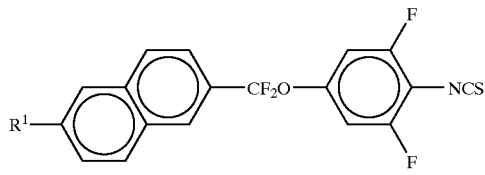
I21
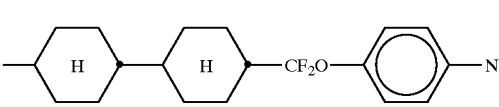
I22
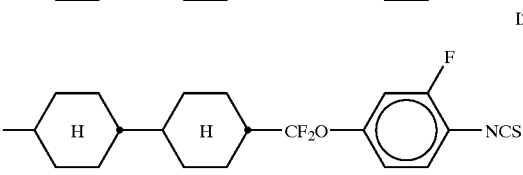
I23
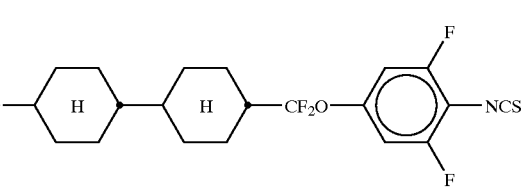
I24
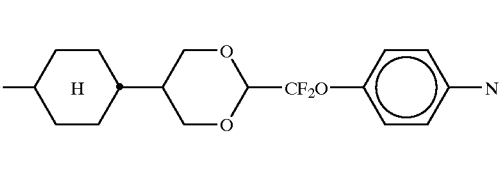
I25
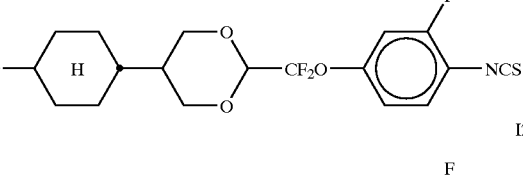
I26
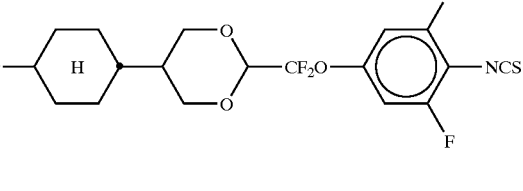
I27

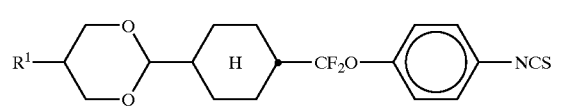
I28
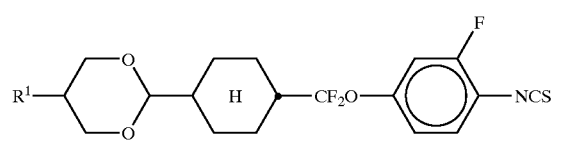
I29
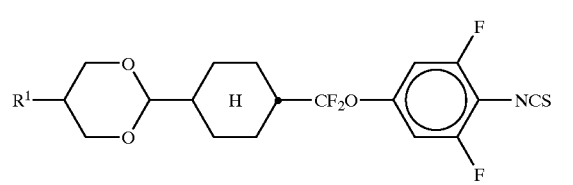
I30
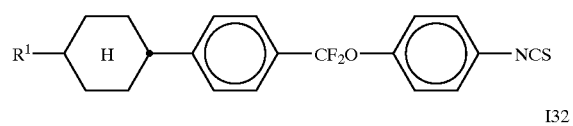
I31
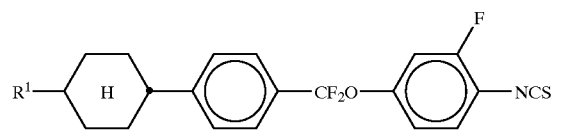
I32
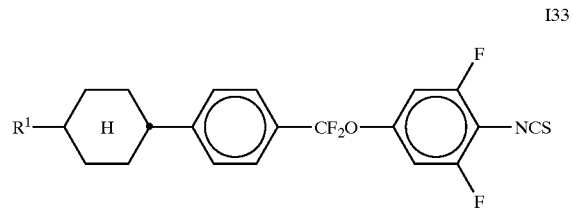
I33
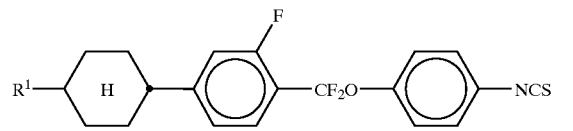
I34
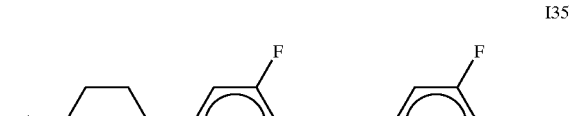
I35
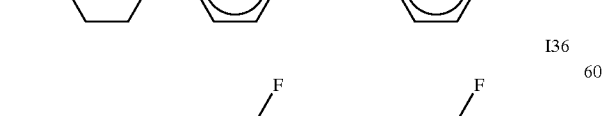
I36
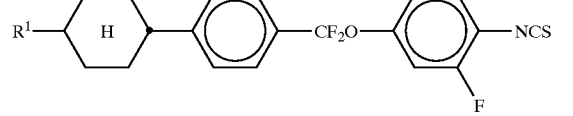
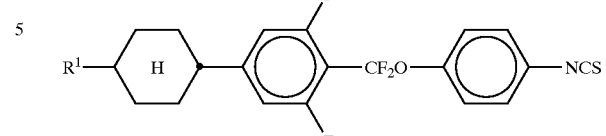
I37
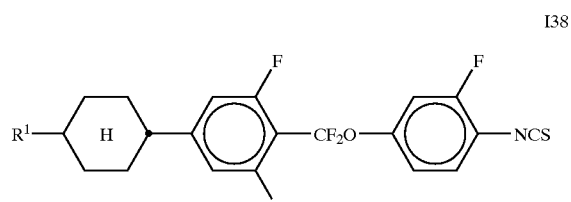
I38
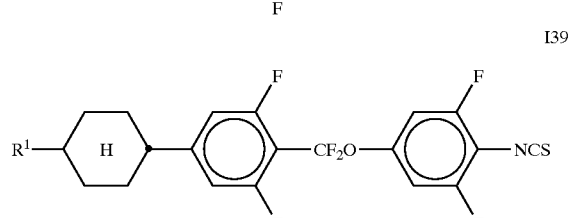
I39
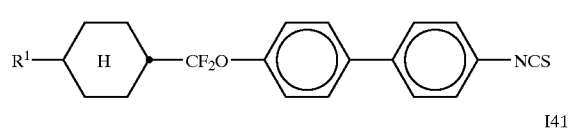
I40
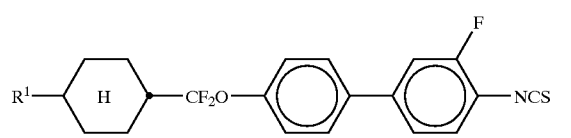
I41
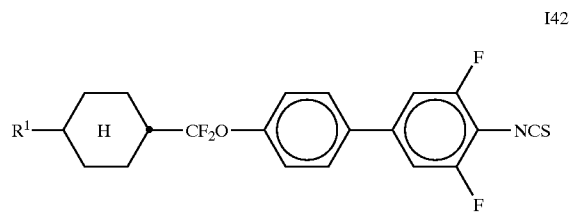
I42
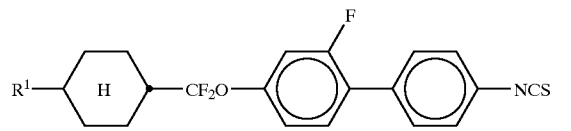
I43
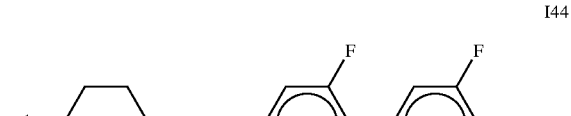
I44
I45
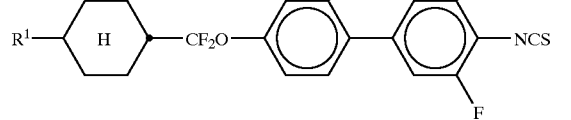

-continued

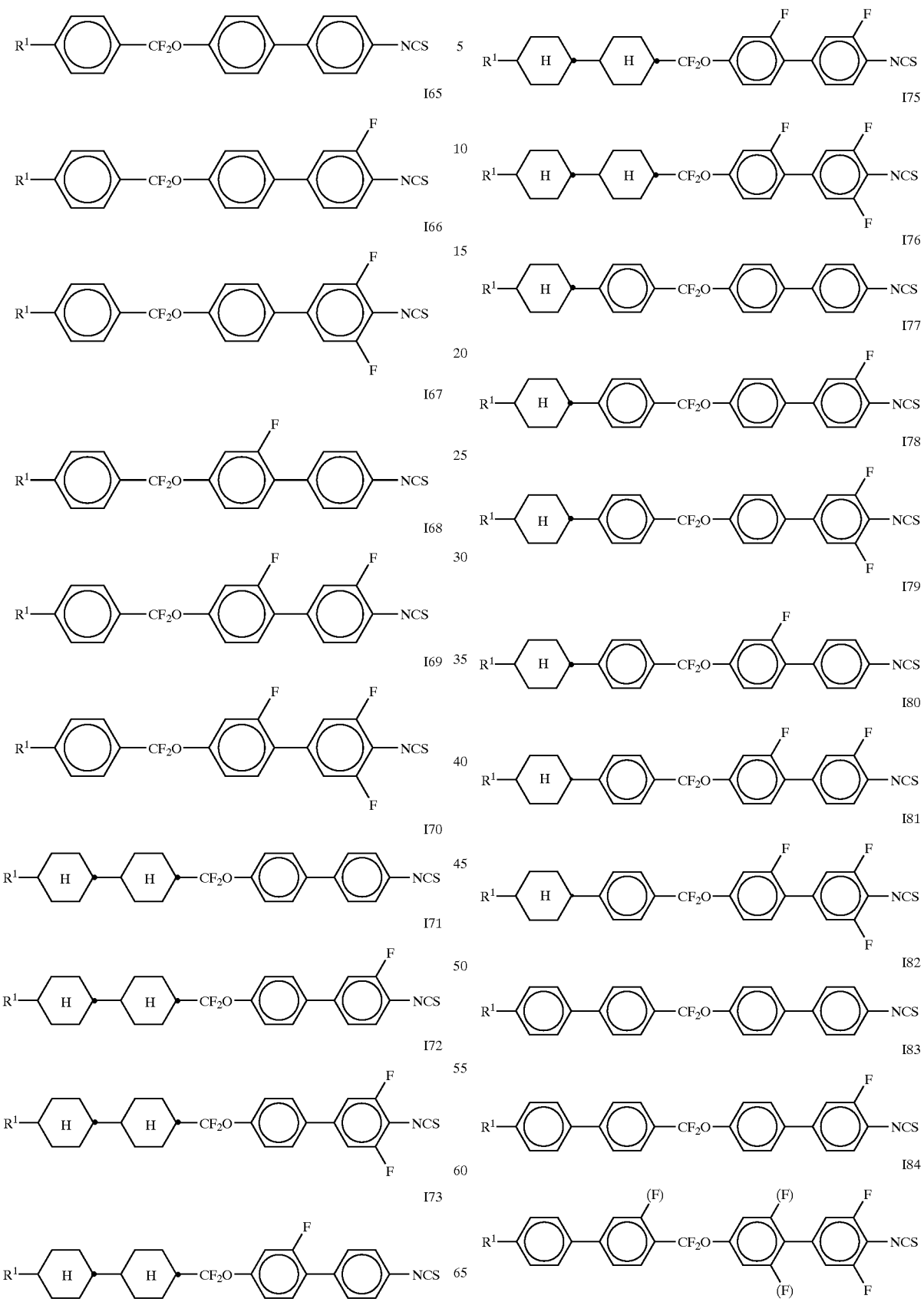

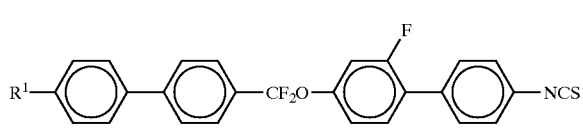
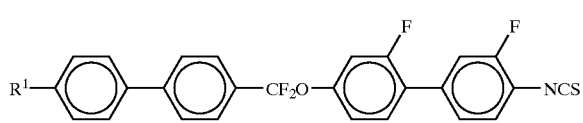
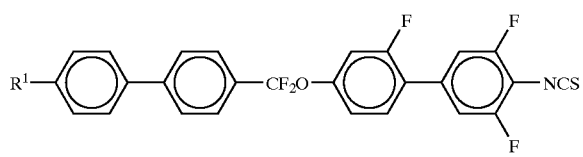
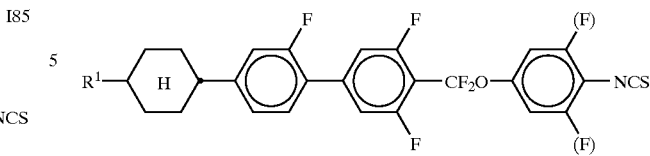

The compounds of the formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

The compounds according to the invention can be prepared, for example, as follows:

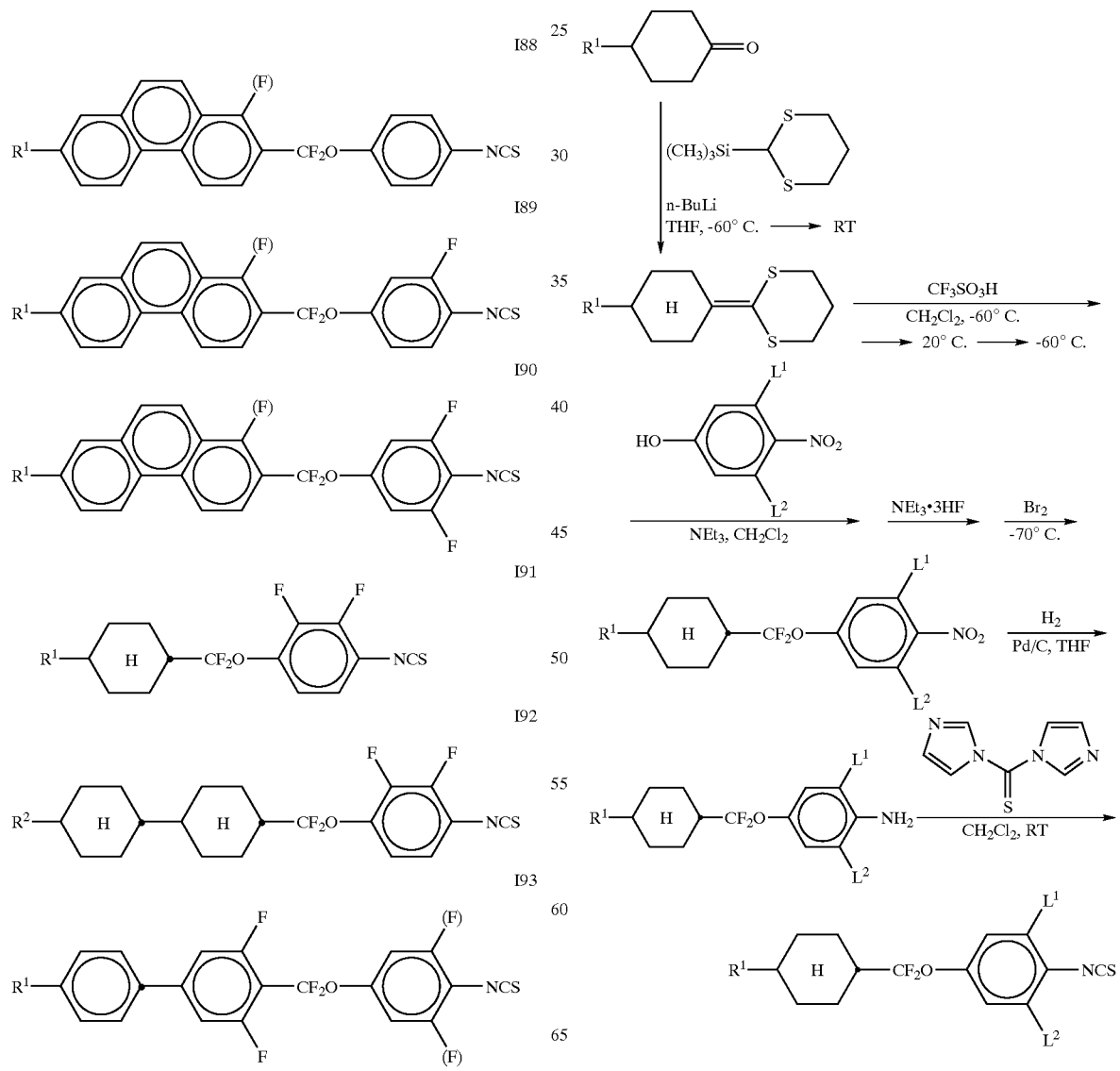

Scheme 2
Scheme 3
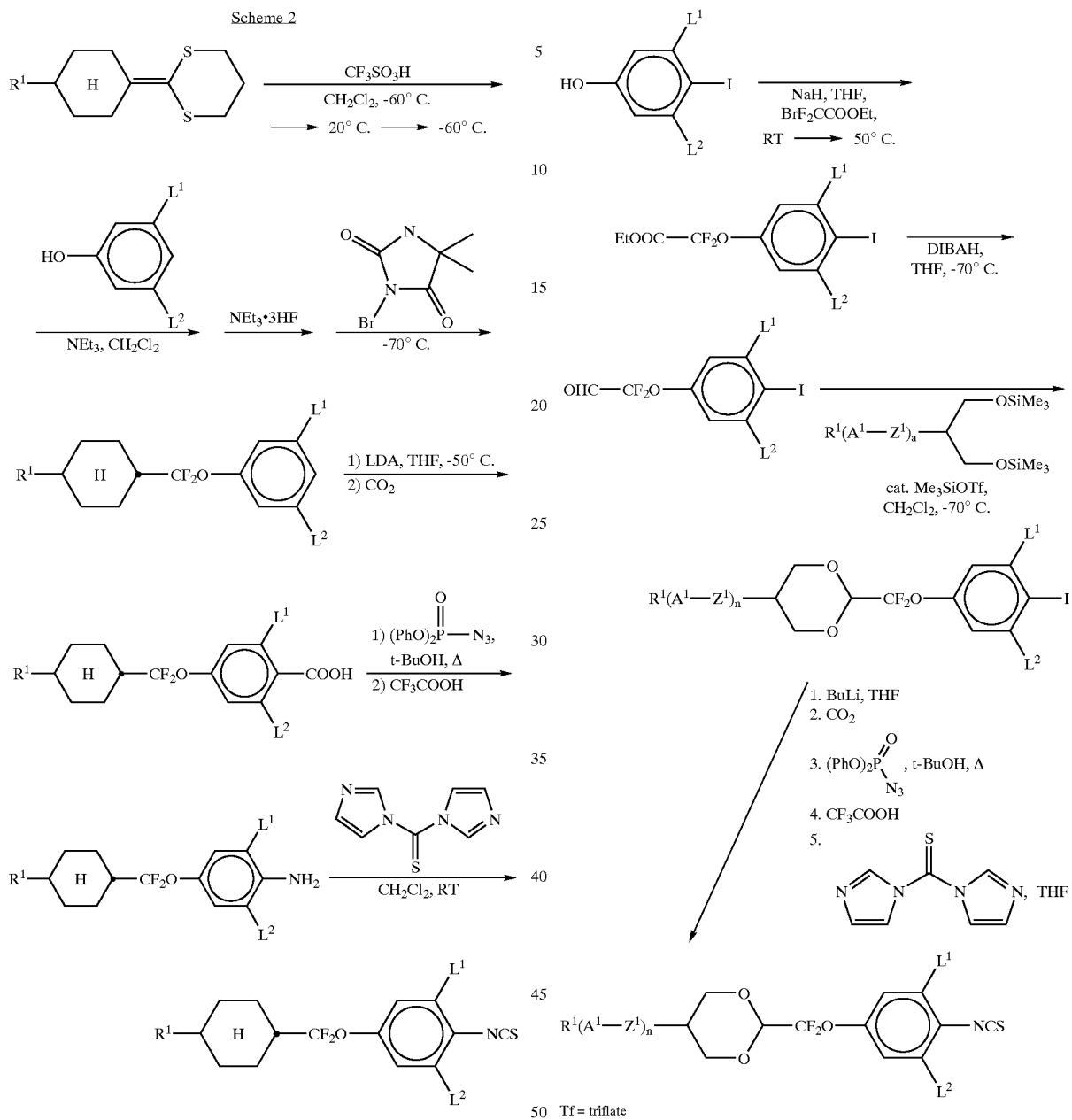
Tf = triflate
Scheme 4
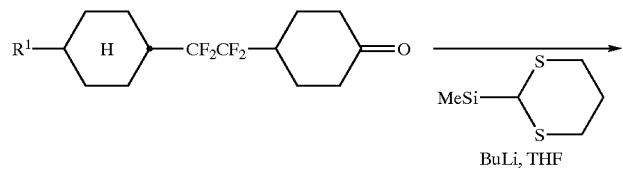

-continued
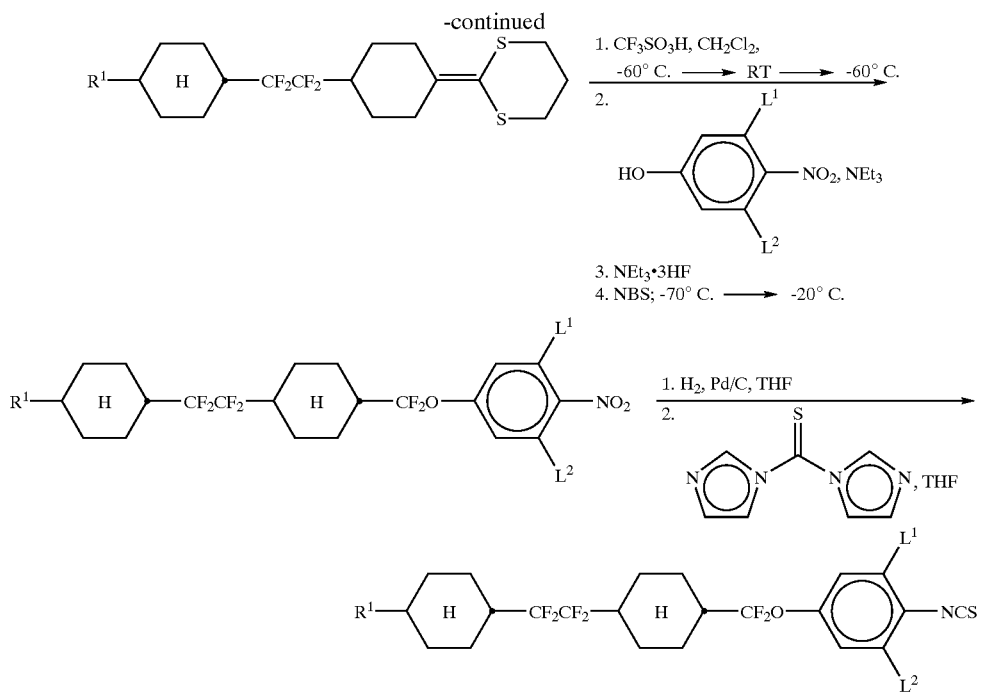
Scheme 5
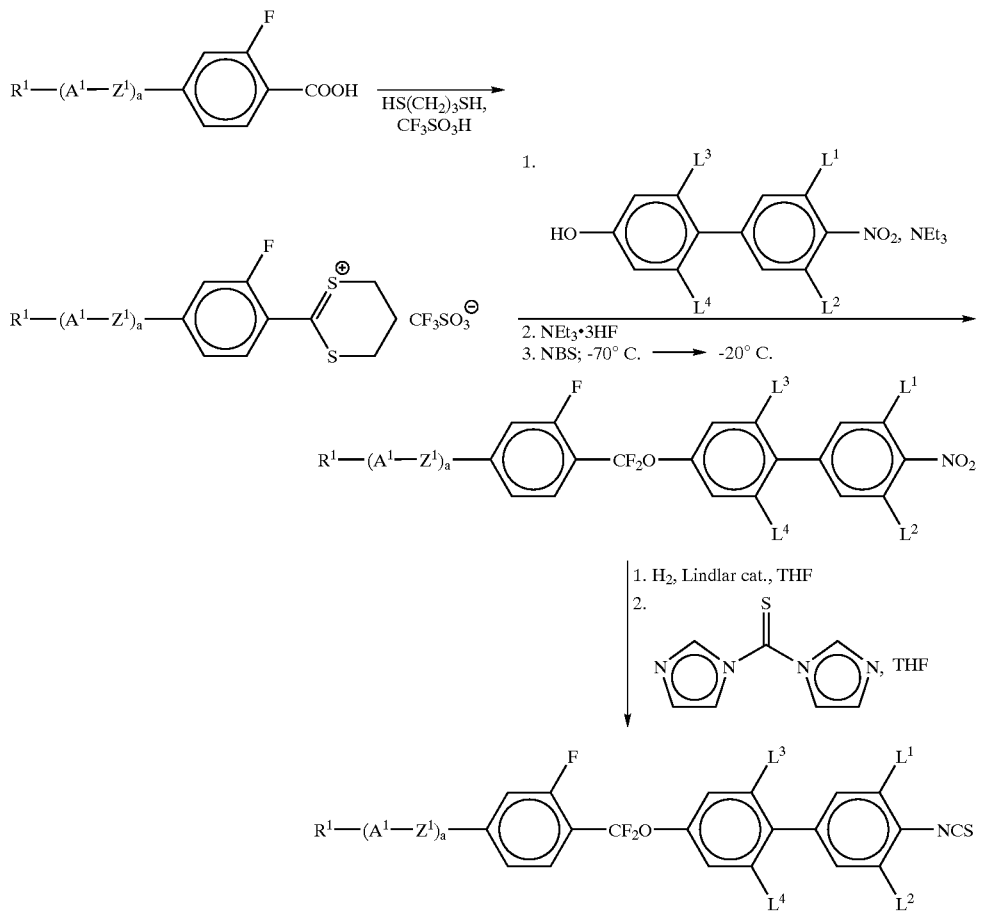

The invention also relates to electro-optical displays (in particular STN or MLC displays having two plane-parallel outer plates, which, together with a frame, form a cell, integrated non-linear elements for switching individual pixels on the outer plates, and a nematic liquid-crystal mixture of positive dielectric anisotropy and high specific resistance which is located in the cell) which contain media of this type, and to the use of these media for electro-optical purposes.

The liquid-crystal mixtures according to the invention enable a significant widening of the available parameter latitude.

The achievable combinations of clearing point, viscosity at low temperature, thermal and UV stability and dielectric anisotropy are far superior to previous materials from the prior art.

The requirement for a high clearing point, a nematic phase at low temperature and a high Δε has hitherto only been achieved to an inadequate extent. Although liquid-crystal mixtures such as, for example, MLC-6476 and MLC-6625 (Merck KgaA, Darmstadt, German) have comparable clearing points and low-temperature stabilities, they have, however, relatively low Δn values and also higher threshold voltages of about ≧1.7 V.

Other mixture systems have comparable viscosities and Δε values, but only have clearing points in the region of 60° C.

The liquid-crystal mixtures according to the invention, while retaining the nematic phase down to −20° C. and preferably down to −30° C., particularly preferably down to −40° C., enable clearing points above 80° C., preferably above 90° C., particularly preferably above 100° C., simultaneously dielectric anisotropy values Δε of ≧4, preferably ≧6, and a high value for the specific resistance to be achieved, enabling excellent STN and MLC displays to be obtained. In particular, the mixtures are characterised by low operating voltages. The TN thresholds are below 1.5 V, preferably below 1.3 V.

It goes without saying that, through a suitable choice of the components of the mixtures according to the invention, it is also possible for higher clearing points (for example above 110°) to be achieved at a higher threshold voltage or lower clearing points to be achieved at lower threshold voltages with retention of the other advantageous properties. At viscosities correspondingly increased only slightly, it is likewise possible to obtain mixtures having greater Δε and thus lower thresholds. The MLC displays according to the invention preferably operate at the first Gooch and Tarry transmission minimum [C. H. Gooch and H. A. Tarry, Electron. Lett. 10, 2–4, 1974; C. H. Gooch and H. A. Tarry, Appl. Phys., Vol. 8, 1575–1584, 1975] are used, where, besides particularly favorable electro-optical properties, such as, for example, high steepness of the characteristic line and low angle dependence of the contrast (German Patent 30 22 818), a lower dielectric anisotropy is sufficient at the same threshold voltage as in an analogous display at the second minimum. This enables significantly higher specific resistances to be achieved using the mixtures according to the invention at the first minimum than in the case of mixtures comprising cyano compounds. Through a suitable choice of the individual components and their proportions by weight, the person skilled in the art is able to set the birefringence necessary for a pre-specified layer thickness of the MLC display using simple routine methods.

The flow viscosity $v_{20}$ at 20° C. is preferably <60 mm²·s⁻¹, particularly preferably <50 mm²·s⁻¹. The nematic phase range is preferably at least 90°, in particular at least 100°. This range preferably extends at least from −30° to +80°.

Measurements of the capacity holding ratio (HR) [S. Matsumoto et al., Liquid Crystals 5, 1320 (1989); K. Niwa et al., Proc. SID Conference, San Francisco, June 1984, p. 304 (1984); G. Weber et al., Liquid Crystals 5, 1381 (1989)] have shown that mixtures according to the invention comprising compounds of the formula I exhibit a significantly smaller decrease in the HR with increasing temperature than, for example, analogous mixtures comprising cyanophenyl-cyclohexanes of the formula

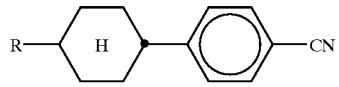

or esters of the formula

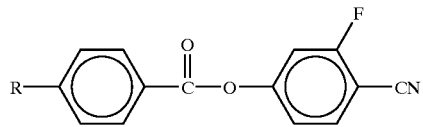

instead of the compounds of the formula I.

The UV stability of the mixtures according to the invention is also considerably better, i.e. they exhibit a significantly smaller decrease in the HR on exposure to UV.

The media according to the invention are preferably based on a plurality of (preferably two, three or more) compounds of the formula 1, i.e. the proportion of these compounds is 5–95%, preferably 10–60% and particularly preferably in the range 15–40%.

The individual compounds of the formulae I to IX and their sub-formulae which can be used in the media according to the invention are either known or they can be prepared analogously to the known compounds.

Preferred embodiments are indicated below:

The medium preferably comprises one, two or three homologous compounds of the formula I, where each homologue is present in the mixture in a maximum proportion of 10%.

The medium comprises compounds of the formula I in which $R^1$ is preferably ethyl and/or propyl, furthermore butyl, pentyl, hexyl and heptyl. Compounds of the formula I having short side chains $R^1$ have a positive effect on the elastic constants, in particular $K_1$, and result in mixtures having particularly low threshold voltages.

Medium additionally comprises one or more compounds selected from the group consisting of the general formulae II to IX:

II

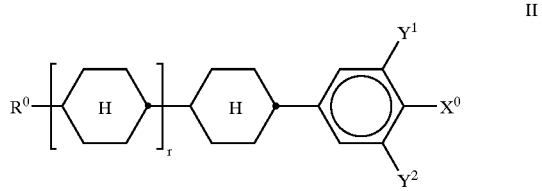

-continued

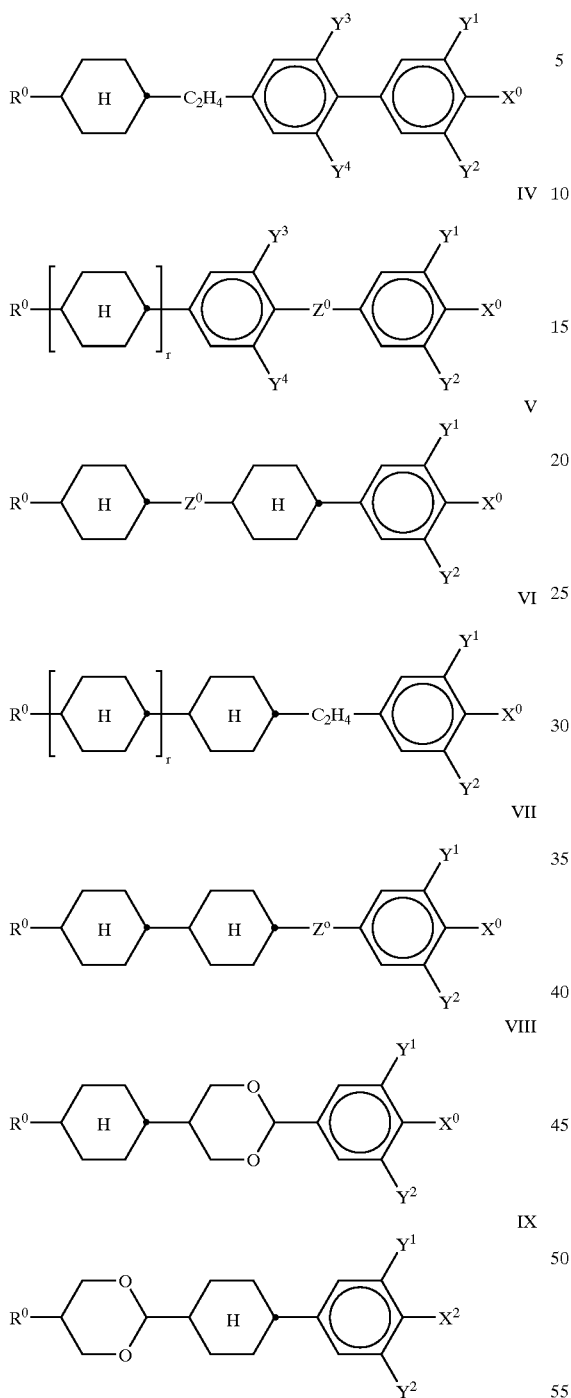

in which the individual radicals have the following meanings:

$R^0$ is n-alkyl, oxaalkyl, fluoroalkyl, alkenyloxy or alkenyl, each having 1 to 9 carbon atoms, $X^0$ is F, Cl, halogenated alkyl, halogenated alkenyl, halogenated alkenyloxy or halogenated alkoxy having 1 to 7 carbon atoms, $Z^0$ is —CH=CH—, —$C_2H_4$—, —$(CH_2)_4$—, —$C_2F_4$—, —CF=CF—, —$CF_2O$—, —$OCF_2$— or —COO—, $Y^1, Y^2,$ $Y^3$ and $Y^4$ are each, independently of one another, H or F, and r is 0 or 1.

The compound of the formula IV is preferably

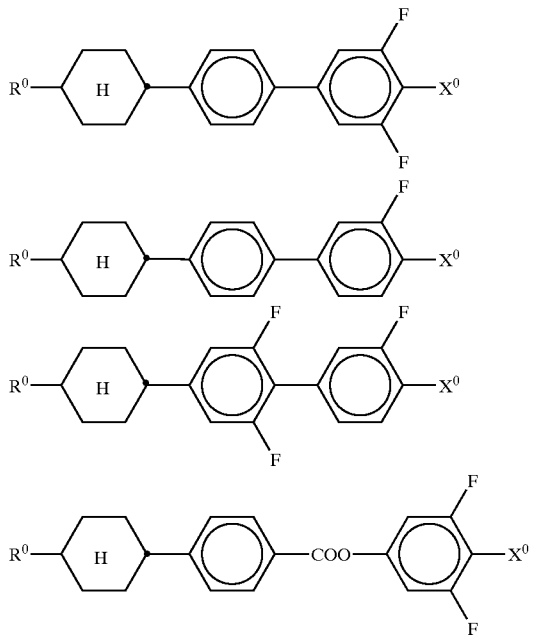

Medium additionally comprises one or more compounds of the formulae

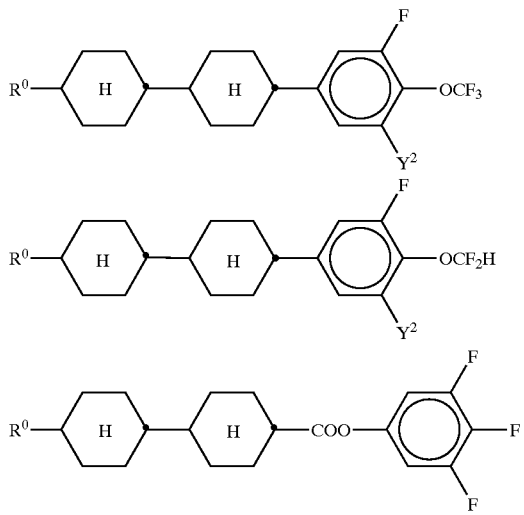

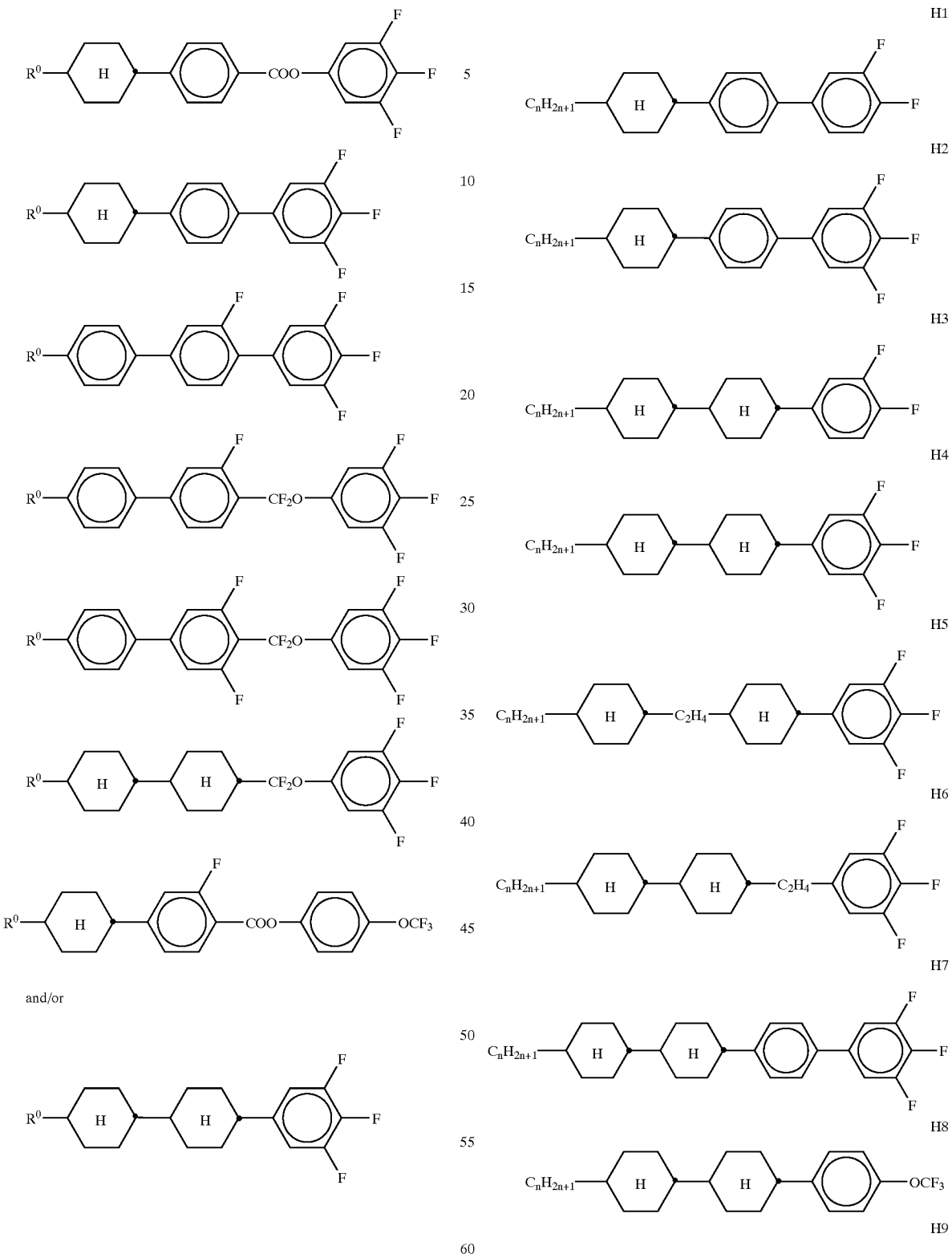
in which $R^0$ and $Y^2$ are as defined above.
The medium preferably comprises one, two or three, furthermore four, homologues of the compounds selected from the group consisting of H1 to H16 (n=1–7):

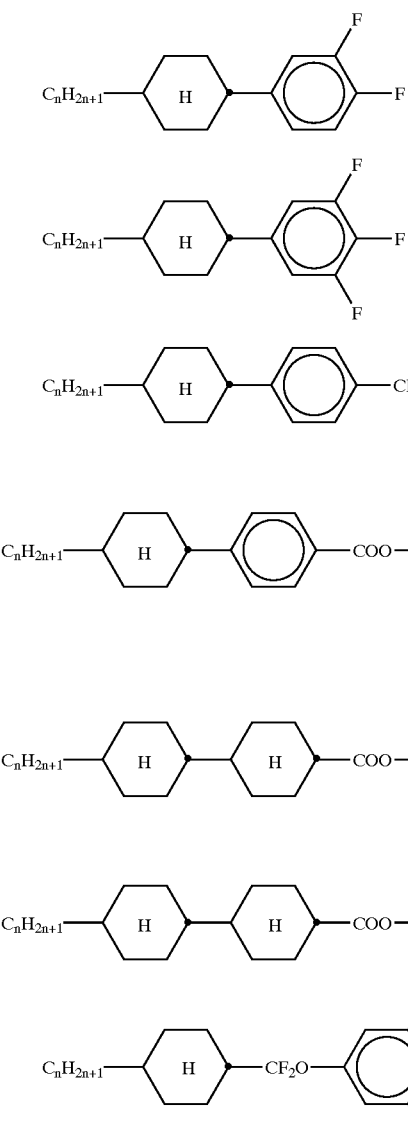

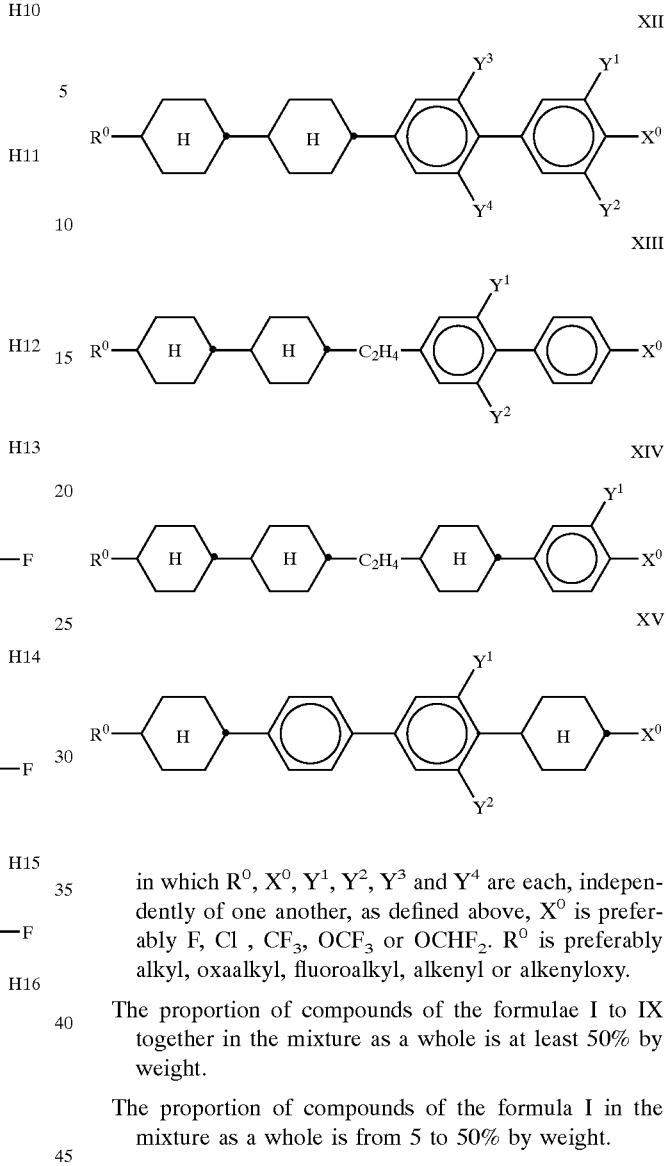

The medium additionally comprises one or more compounds selected from the group consisting of the general formulae X to XV:

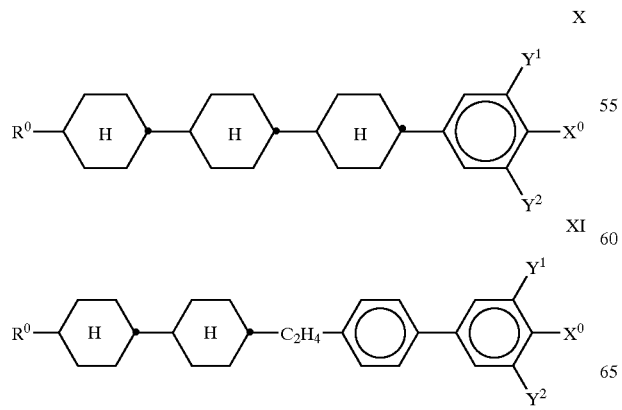

in which $R^0$, $X^0$, $Y^1$, $Y^2$, $Y^3$ and $Y^4$ are each, independently of one another, as defined above, $X^0$ is preferably F, Cl, $CF_3$, $OCF_3$ or $OCHF_2$. $R^0$ is preferably alkyl, oxaalkyl, fluoroalkyl, alkenyl or alkenyloxy.

The proportion of compounds of the formulae I to IX together in the mixture as a whole is at least 50% by weight.

The proportion of compounds of the formula I in the mixture as a whole is from 5 to 50% by weight.

The proportion of compounds of the formulae II to IX in the mixture as a whole is from 30 to 70% by weight.

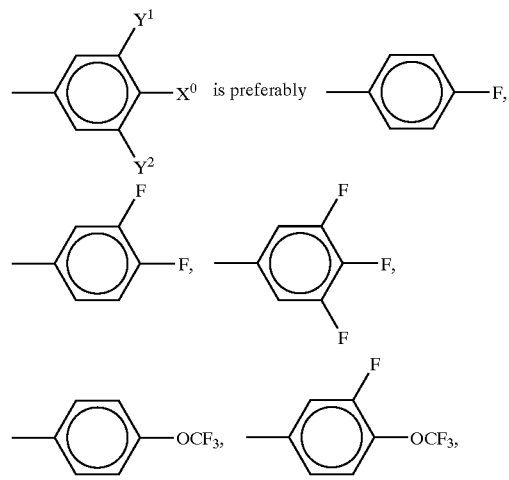

-continued

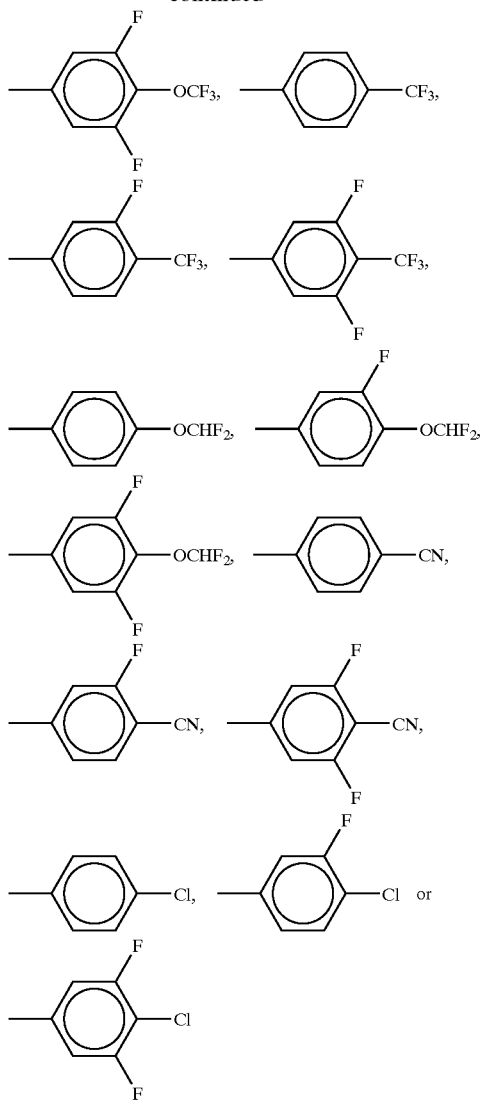

The medium comprises compounds of the formulae II, III, IV, V, VI, VII, VIII and/or IX.

$R^0$ is straight-chain alkyl or alkenyl having from 2 to 7 carbon atoms.

The medium essentially consists of compounds of the formulae I to XV.

The medium comprises further compounds, preferably selected from the following group consisting of the general formulae XVI to XX:

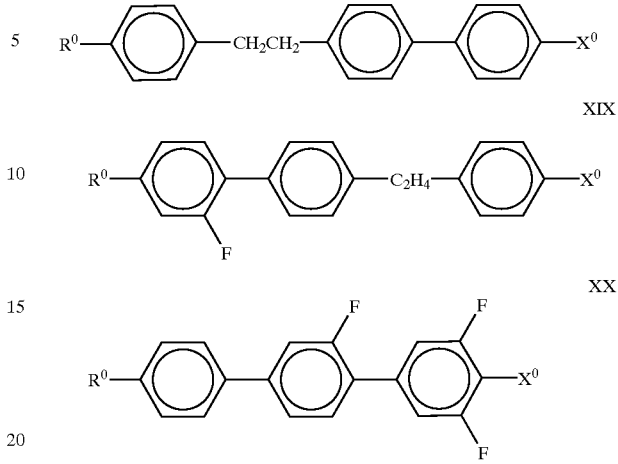

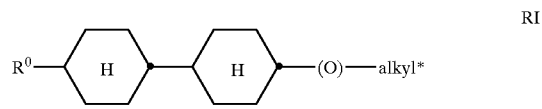

in which $R^0$ and $X^0$ are as defined above, and the 1,4-phenylene rings may be substituted by CN, chorine or fluorine. The 1,4-phenylene rings are preferably monosubstituted or polysubstituted by fluorine atoms.

The medium comprises further compounds, preferably selected from the following group consisting of the formulae RI to RVIII:

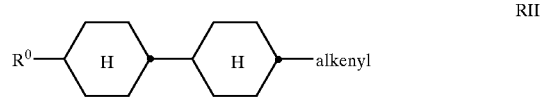

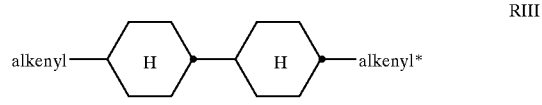

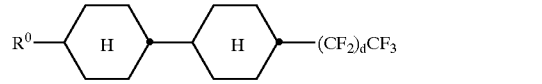

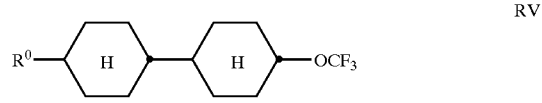

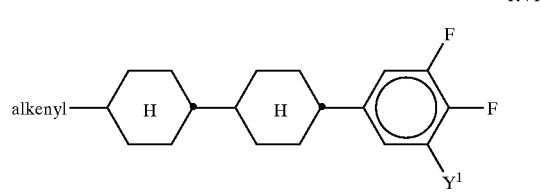

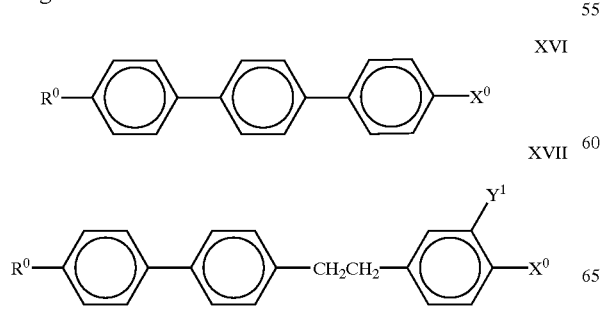

-continued

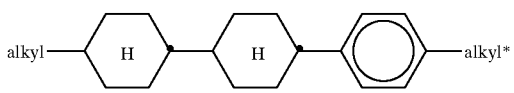
RVIII in which
R⁰ is n-alkyl, oxaalkyl, fluoroalkyl, alkenyloxy or alkenyl, each having 1 to 9 carbon atoms,
d is 0, 1 or 2,
$Y^1$ is H or F,
alkyl and
alkyl* are each, independently of one another, a straight-chain or branched alkyl radical having 1–9 carbon atoms,
alkenyl and
alkenyl* are each, independently of one another, a straight-chain or branched alkenyl radical having 2 to 9 carbon atoms.

The medium preferably comprises one or more compounds of the formulae

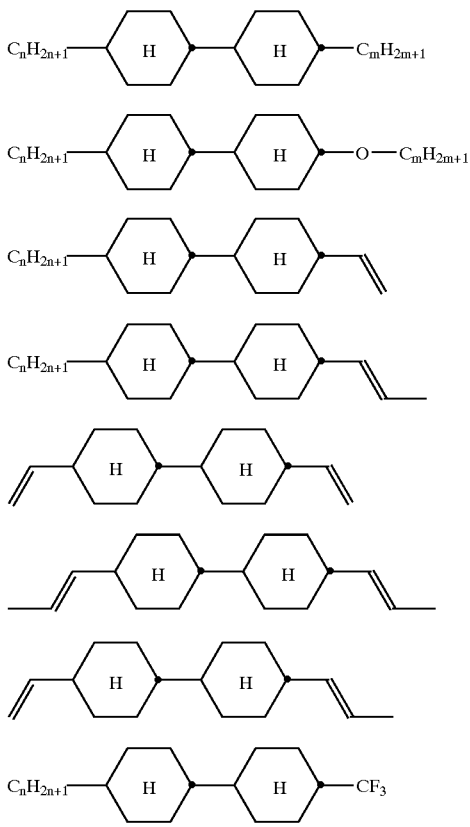

RIa
RIb
RIIa
RIIb
RIIIa
RIIIb
RIIIc
RIVa in which n and m are each an integer from 1–9.
The I: (II+III+IV+V+VI+VII+VIII+IX) weight ratio is preferably from 1:10 to 10:1.
The medium essentially consists of compounds selected from the group consisting of the general formulae I to XV.

It has been found that even a relatively small proportion of compounds of the formula I mixed with conventional liquid-crystal materials, but in particular with one or more compounds of the formulae II, III, IV, V, VI, VII, VIII and/or IX, results in a significant lowering of the threshold voltage and in low birefringence values, with broad nematic phases with low smectic-nematic transition temperatures being observed at the same time, improving the shelf life. The compounds of the formulae I to IX are colorless, stable and readily miscible with one another and with other liquid-crystalline materials.

The term "alkyl" or "alkyl*" covers straight-chain and branched alkyl groups having 1–9 carbon atoms, in particular the straight-chain groups methyl, ethyl, propyl, butyl, pentyl, hexyl and heptyl. Groups having 2–5 carbon atoms are generally preferred.

The term "alkenyl" or "alkenyl*" covers straight-chain and branched alkenyl groups having 2 to 9 carbon atoms, in particular the straight-chain groups. Preferred alkenyl groups are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4-alkenyl. Examples of particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably covers straight-chain groups having a terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" preferably covers straight-chain radicals of the formula $C_nH_{2n+1}$—O—$(CH_2)_m$, in which n and m are each, independently of one another, from 1 to 6. n is preferably =1 and m is preferably from 1 to 6.

Through a suitable choice of the meanings of $R^0$ and $X^0$, the addressing times, the threshold voltage, the steepness of the transmission characteristic lines, etc., can be modified in the desired manner. For example, 1 E-alkenyl radicals, 3E-alkenyl radicals, 2E-alkenyloxy radicals and the like generally result in shorter addressing times, improved nematic tendencies and a higher ratio of the elastic constants $k_{33}$ (bend) and $k_{11}$ (splay) compared with alkyl or alkoxy radicals. 4-alkenyl radicals, 3-alkenyl radicals and the like generally give lower threshold voltages and smaller values of $k_{33}/k_{11}$ compared with alkyl and alkoxy radicals.

A —$CH_2CH_2$— group in $Z^1$ generally results in higher values of $k_{33}/k_{11}$ compared with a single covalent bond. Higher values of $k_{33}/k_{11}$ facilitate, for example, flatter transmission characteristic lines in TN cells with a 90° twist (in order to achieve grey shades) and steeper transmission characteristic lines in STN, SBE and OMI cells (greater multiplexability), and vice versa.

The optimum mixing ratio of the compounds of the formulae I and II+III+IV+V+VI+VII+VII+IX depends substantially on the desired properties, on the choice of the components of the formulae I, II, III, IV, V, VI, VII, VIII and/or IX, and the choice of any other components that may be present. Suitable mixing ratios within the range given above can easily be determined from case to case.

The total amount of compounds of the formulae I to XV in the mixtures according to the invention is not crucial. The mixtures can therefore comprise one or more further components for the purposes of optimizing various properties. However, the observed effect on the addressing times and the threshold voltage is generally greater, the higher the total concentration of compounds of the formulae I to XV.

In a particularly preferred embodiment, the media according to the invention comprise compounds of the formulae II to IX (preferably II and/or III) in which $X^0$ is $OCF_3$, $OCHF_2$, F, OCH=CF$_2$, OCF=CF$_2$, OCF$_2$CHFCF$_3$ or OCF$_2$—CF$_2$H. A favourable synergistic effect with the compounds of the formula I results in particularly advantageous properties.

The construction of the MLC display according to the invention from polarisers, electrode base plates and surface-treated electrodes corresponds to the conventional construction for displays of this type. The term "conventional construction" is broadly drawn here and also covers all derivatives and modifications of the MLC display, in particular including matrix display elements based on poly-Si TFT or MIM.

A significant difference between the displays according to the invention and the conventional displays based on the twisted nematic cell consists, however, in the choice of the liquid-crystal parameters of the liquid-crystal layer.

The liquid-crystal mixtures which can be used in accordance with the invention are prepared in a manner conventional per se. In general, the desired amount of the components used in the lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing.

The dielectrics may also comprise further additives known to the person skilled in the art and described in the literature, such as, for example, stabilisers and antioxidants. For example, 0–15% of pleochroic dyes or chiral dopants can be added.

C denotes a crystalline phase, S a smectic phase, $S_C$ a smectic C phase, $S_B$ a smectic B phase, N a nematic phase and I the isotropic phase.

$V_{10}$ denotes the voltage for 10% transmission (viewing angle perpendicular to the plate surface). $t_{on}$ denotes the switch-on time and $t_{off}$ the switch-off time at an operating voltage corresponding to 2 times the value of $V_{10}$. $\Delta n$ denotes the optical anisotropy and $n_0$ the refractive index. $\Delta\epsilon$ denotes the dielectric anisotropy ($\Delta\epsilon=\epsilon_\|-\epsilon_\perp$, where $\epsilon_\|$ denotes the dielectric constant parallel to the longitudinal molecular axes and $\epsilon_\perp$ denotes the dielectric constant perpendicular thereto). The electro-optical data were measured in a TN cell at the 1st minimum (i.e. at a d·$\Delta n$ value of 0.5) at 20° C., unless expressly stated otherwise. The optical data were measured at 20° C., unless expressly stated otherwise.

The entire disclosure(s) of all applications, patents and publications, cited above or below, and of corresponding German Application 10136188.2, filed Jul. 25, 2001, is hereby incorporated by reference.

EXAMPLES

In the present application and in the examples below, the structures of the liquid-crystal compounds are indicated by means of acronyms, the transformation into chemical formulae taking place in accordance with Tables A and B below. All radicals $C_nH_{2n+1}$ and $C_mH_{2m+1}$ are straight-chain alkyl radicals having n and m carbon atoms respectively; n and m are in each case, independently of one another, 1, 2, 3, 4, 5, 6, 7, 8, 9, 10, 11, 12, 13, 14 or 15. The coding in Table B is self-evident. In Table A, only the acronym for the parent structure is indicated. In individual cases, the acronym for the parent structure is followed, separated by a dash, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nF.F.F | $C_nH_{2n+1}$ | F | F | F |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_2H_{2s}$— | CN | H | H |
| nAm | $C_nH_{2n+1}$ | COOC$_m$H$_{2m+1}$ | H | H |
| nOCCF$_2$.F.F | $C_nH_{2n+1}$ | OCH$_2$CF$_2$H | F | F |

Preferred mixture components are shown in Tables A and B.

TABLE A

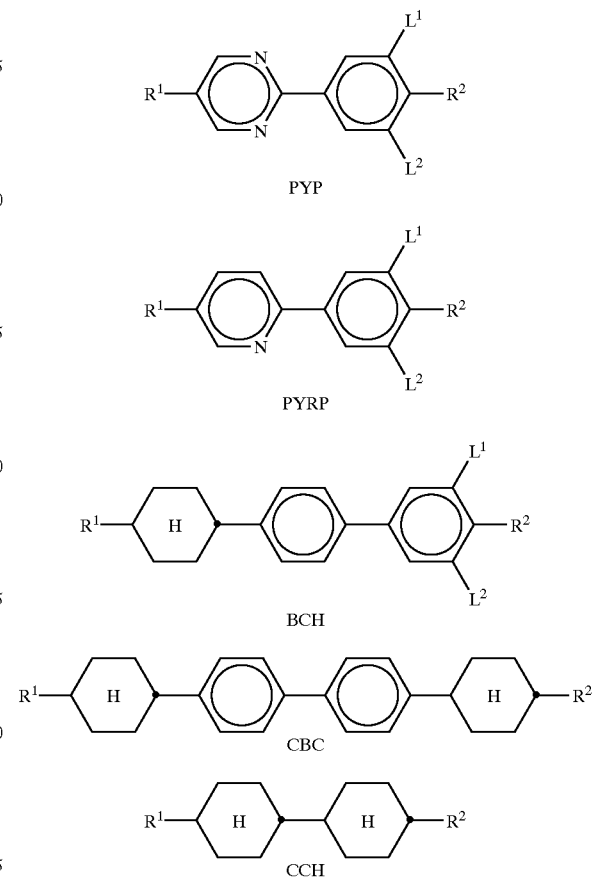

TABLE A-continued
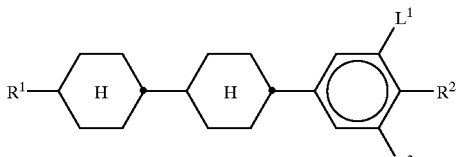
CCP
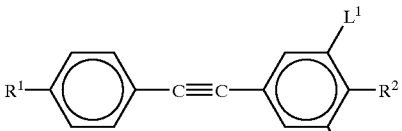
CPTP
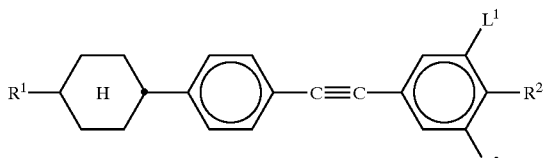
CEPTP
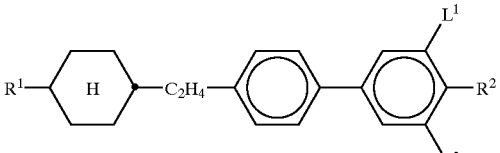
ECCP
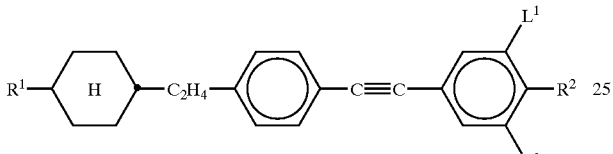
CECP
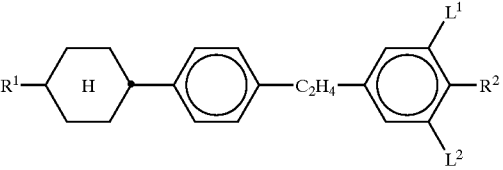
EPCH
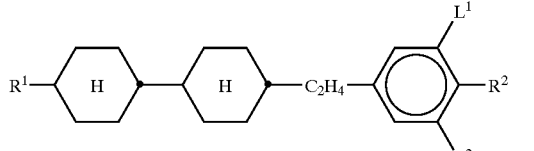
PCH
TABLE A-continued
PTP
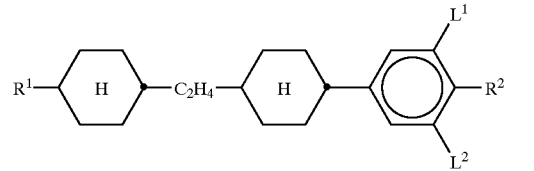
BECH
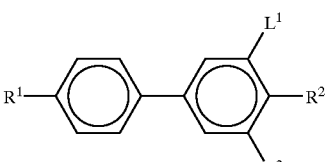
EBCH
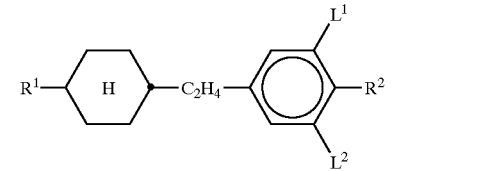
CPC
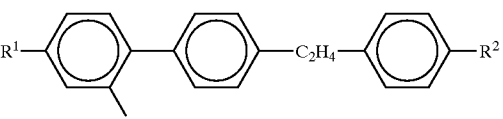
B
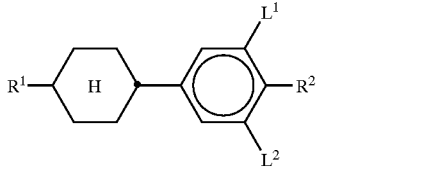
FET-nF
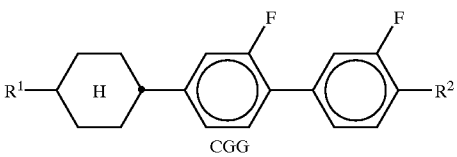
CGG
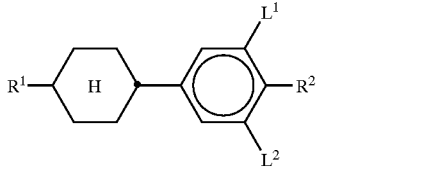
CGU TABLE A-continued
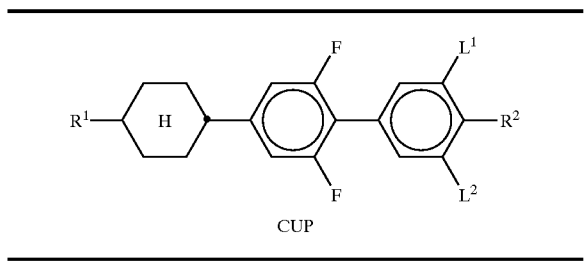
CUP
TABLE B
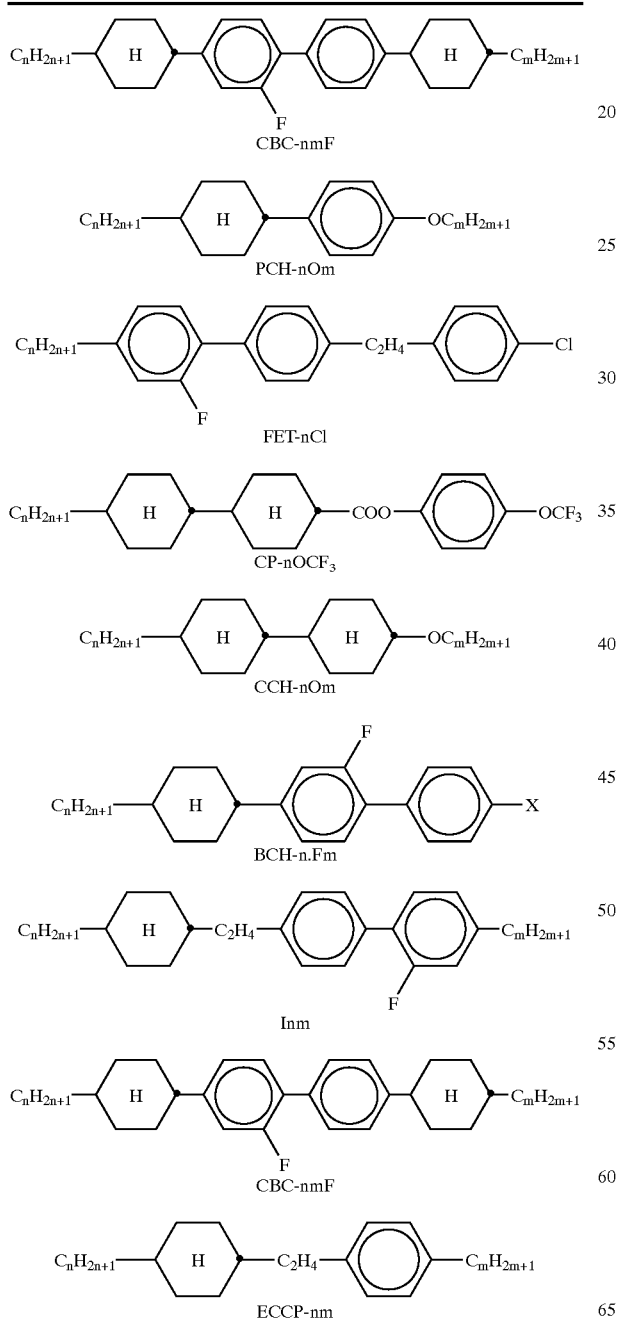
TABLE B-continued
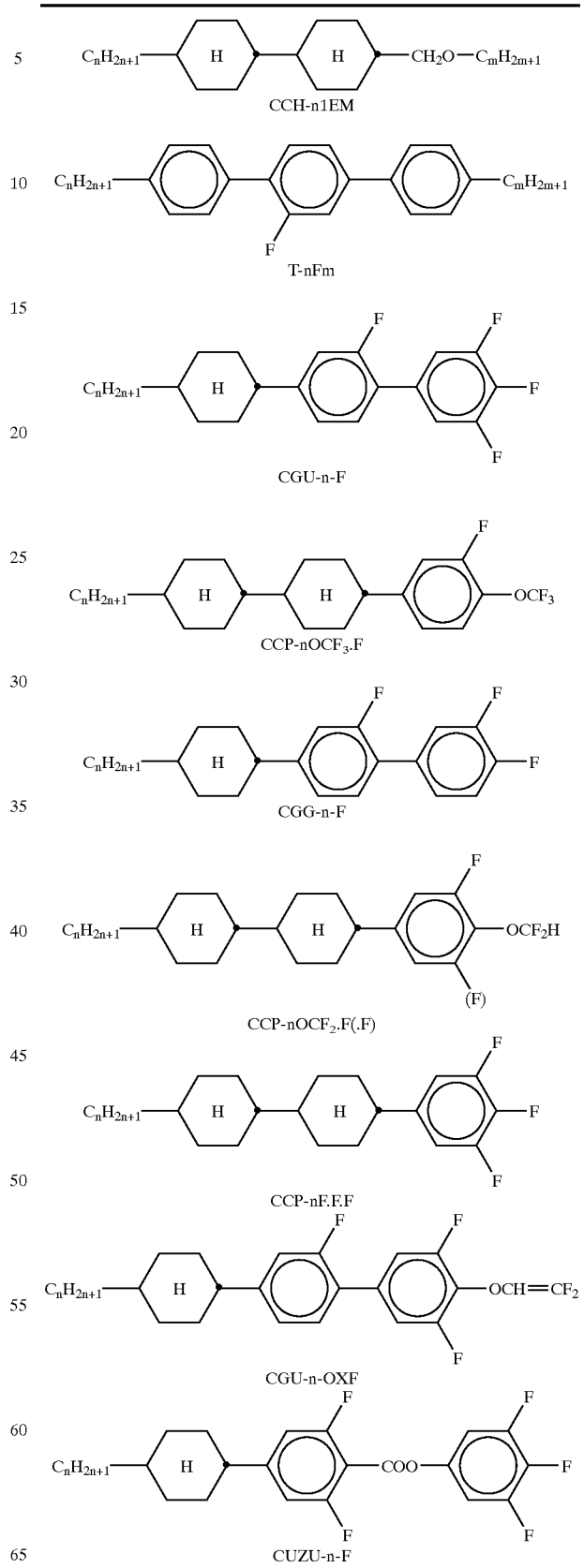

TABLE B-continued
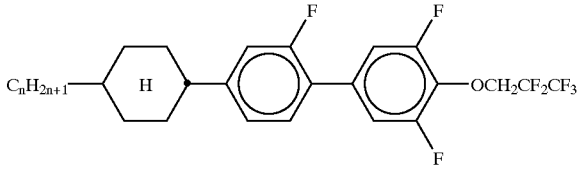
CGU-n-O1DT
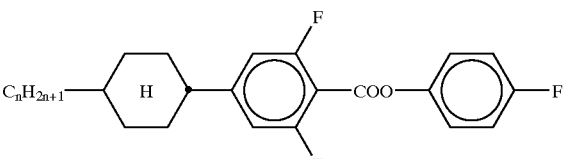
CCZU-n-F
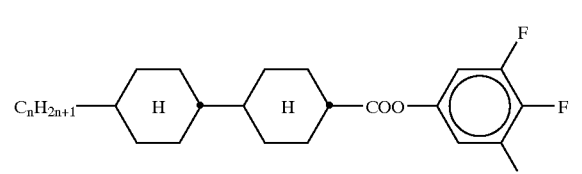
CC-n-V1
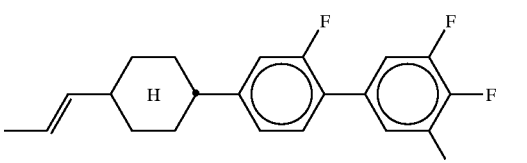
CC-n-V
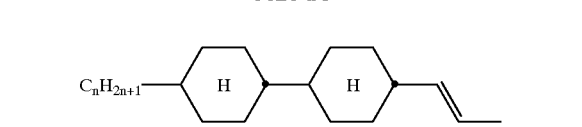
CCP-nOCF₃
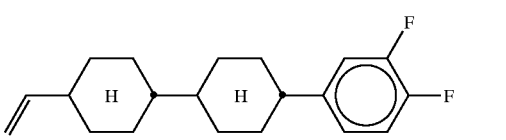
BCH-nF.F.F
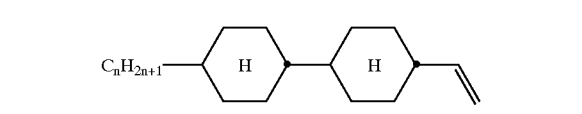
CWCQU-n-F
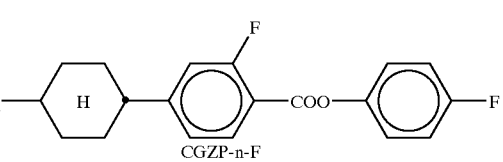
CCOC-n-m
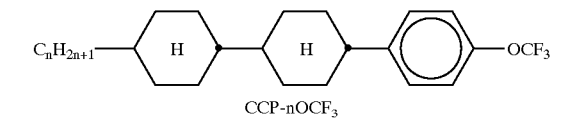
CGZU-n-F
TABLE B-continued
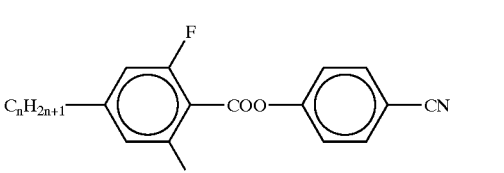
CUZP-n-F
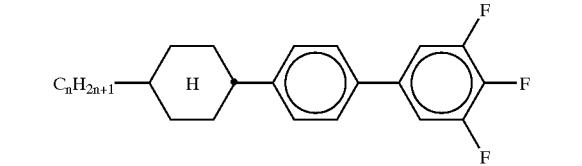
CGU-1V-F
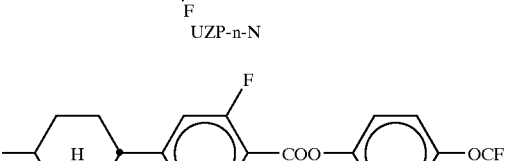
CCG-V-F
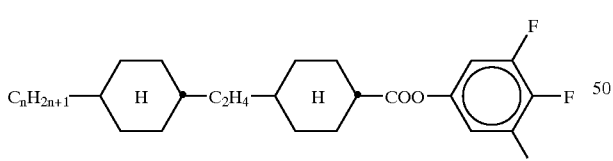
CGZP-n-F
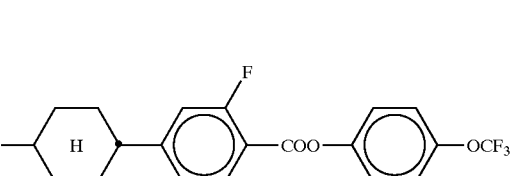
UZP-n-N
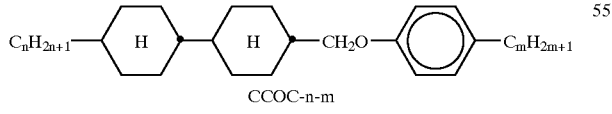
CGZP-n-OT
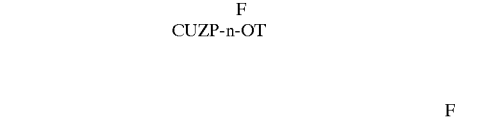
CUZP-n-OT
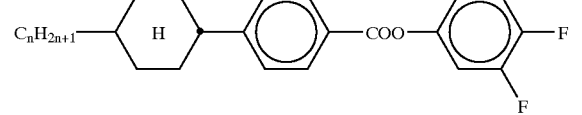
CCQU-n-F TABLE B-continued
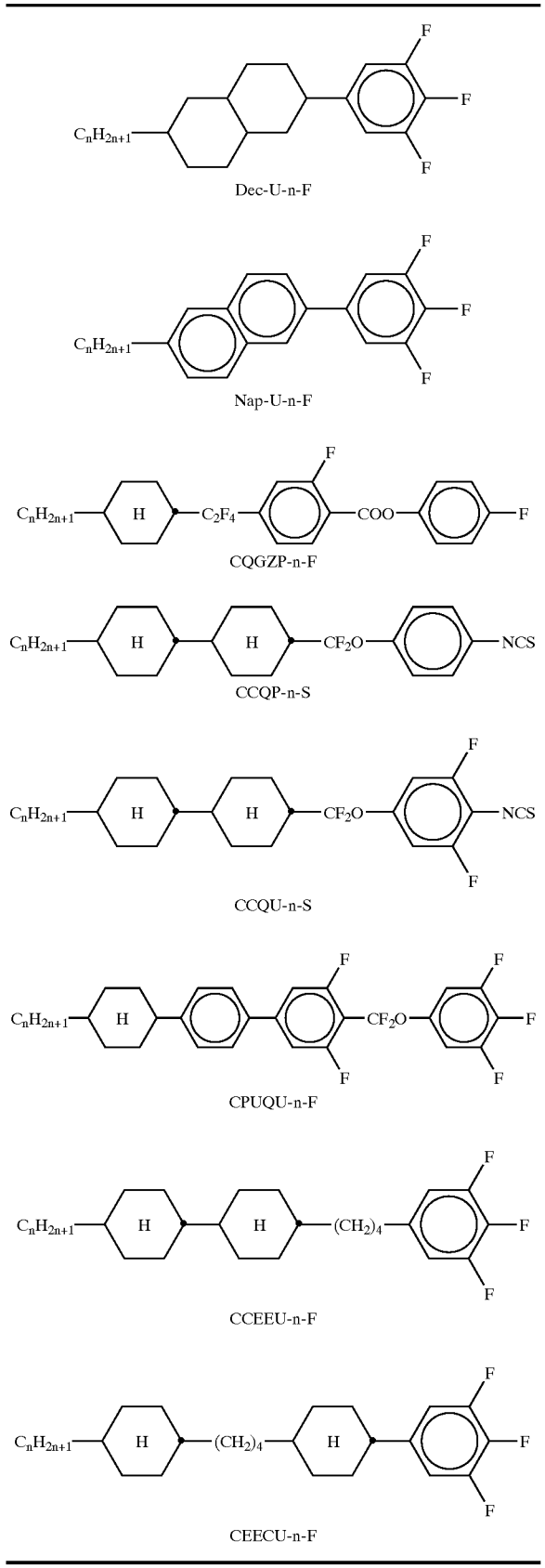
TABLE C
Table C shows possible dopants which are generally added to the mixtures according to the invention.
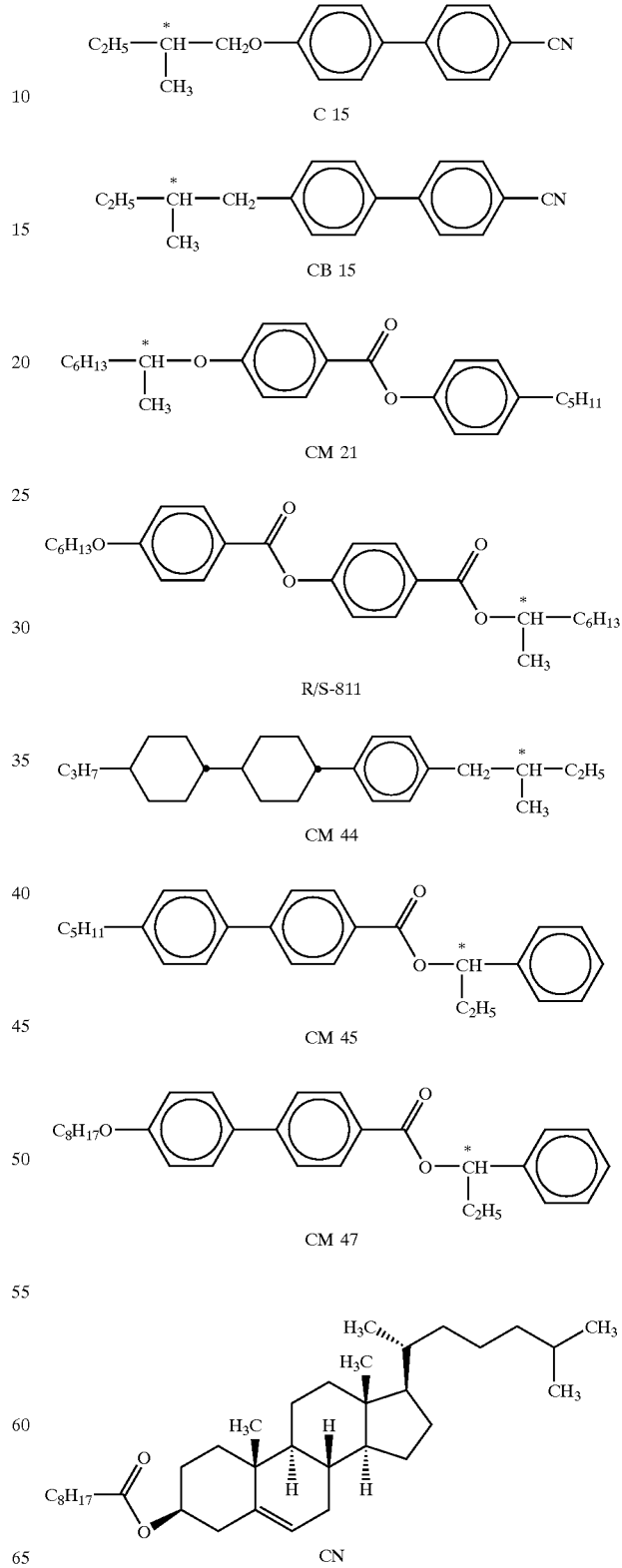

TABLE C-continued
Table C shows possible dopants which are generally added to the mixtures according to the invention.
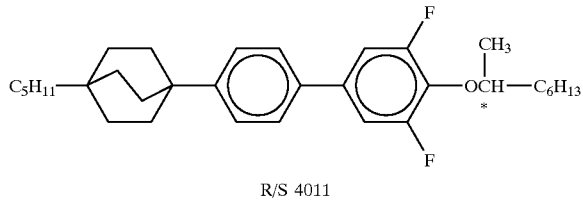
R/S 4011
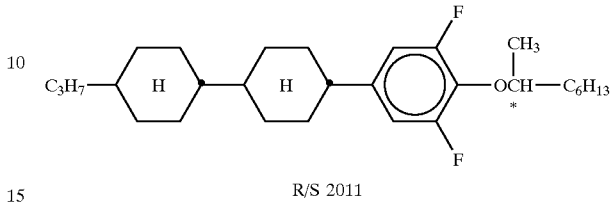
R/S 2011
TABLE D
Stabilisers which can be added, for example, to the mixtures according to the invention are mentioned below.
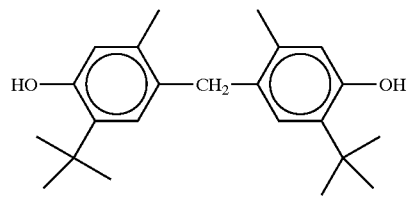
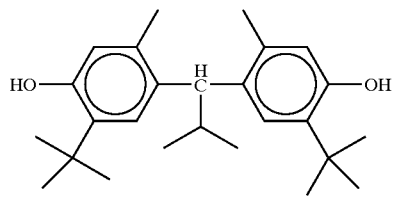
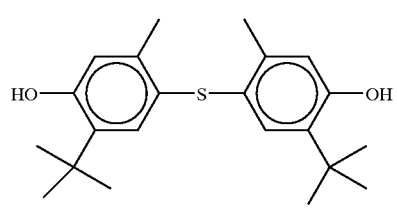
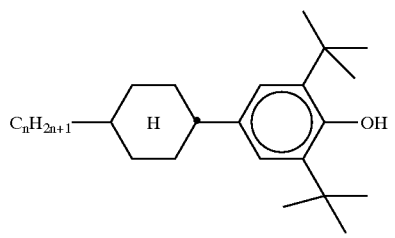
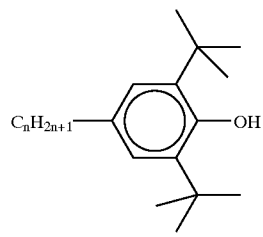
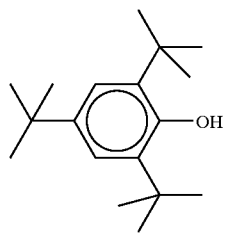
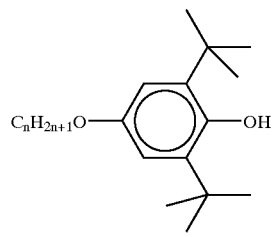
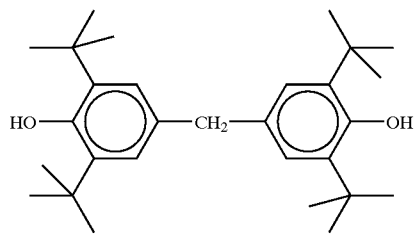

TABLE D-continued
Stabilisers which can be added, for example, to the mixtures according to the invention are mentioned below.
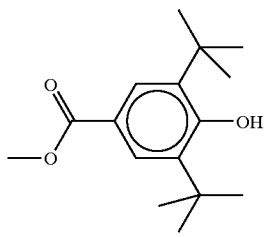
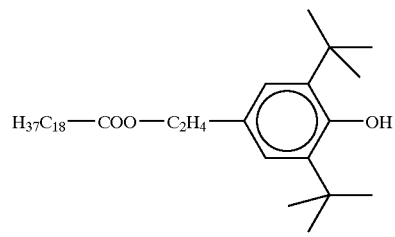
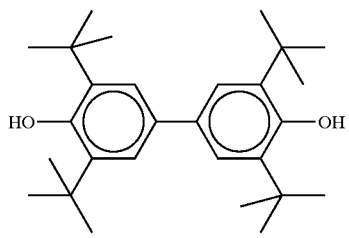
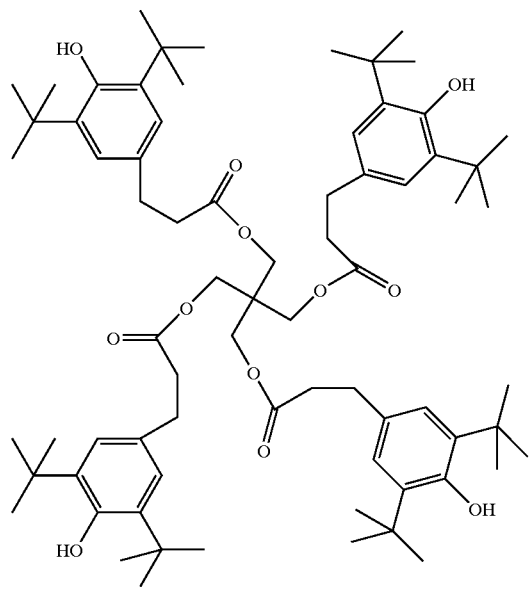
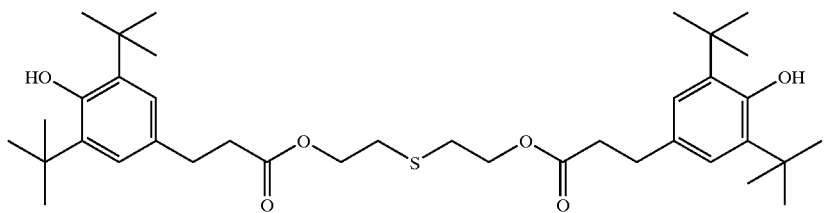
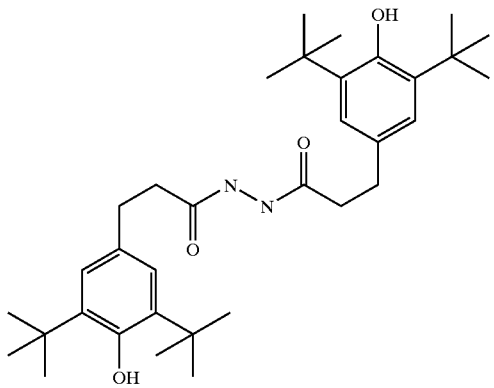
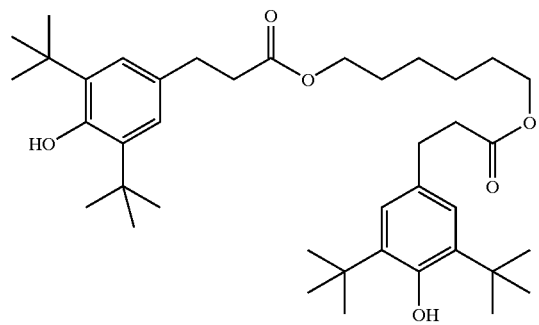

TABLE D-continued
Stabilisers which can be added, for example, to the mixtures according to the invention are mentioned below.
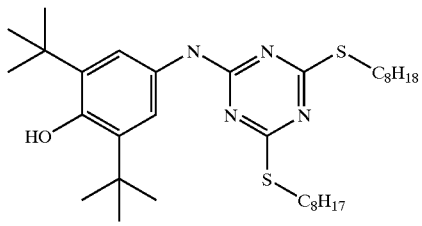
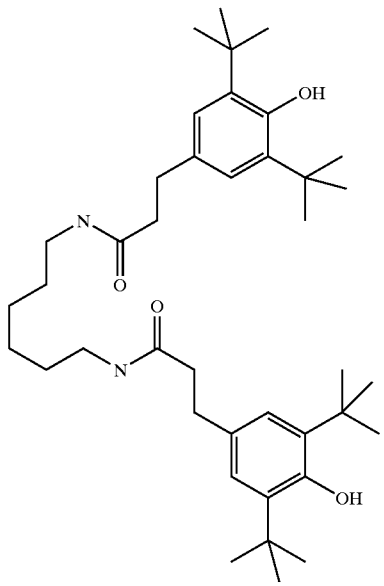
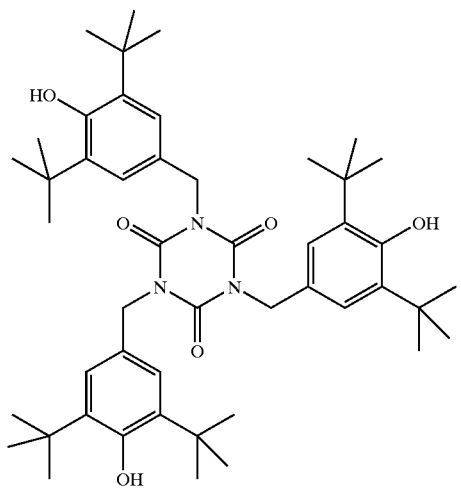
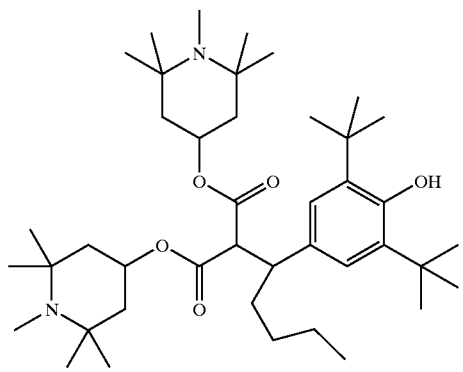
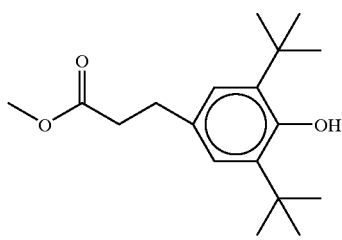
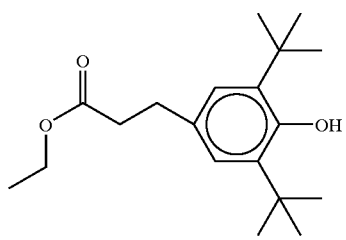
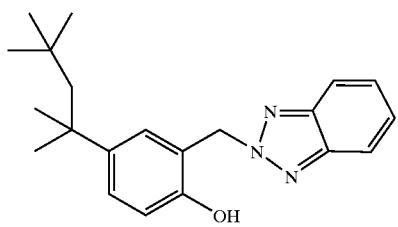

TABLE D-continued
Stabilisers which can be added, for example, to the mixtures according to the invention are mentioned below.
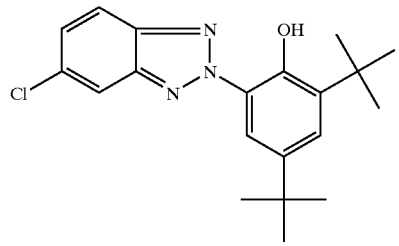
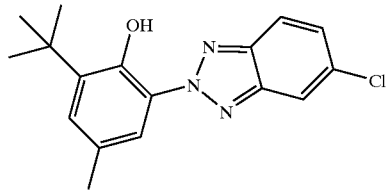
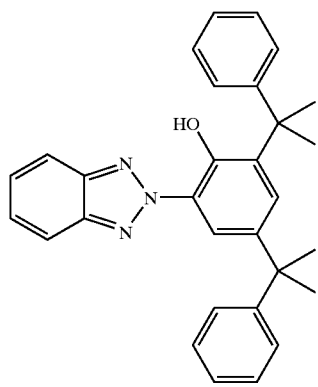
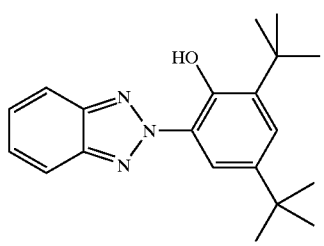
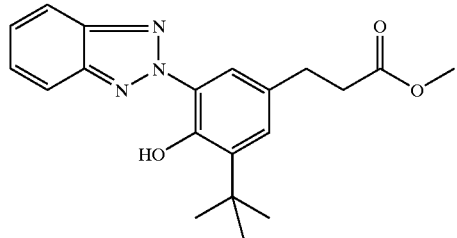
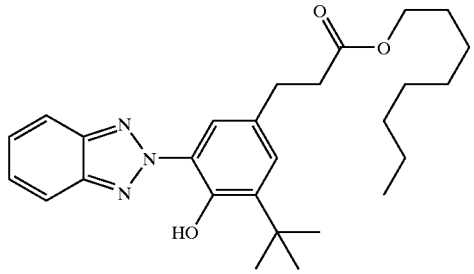
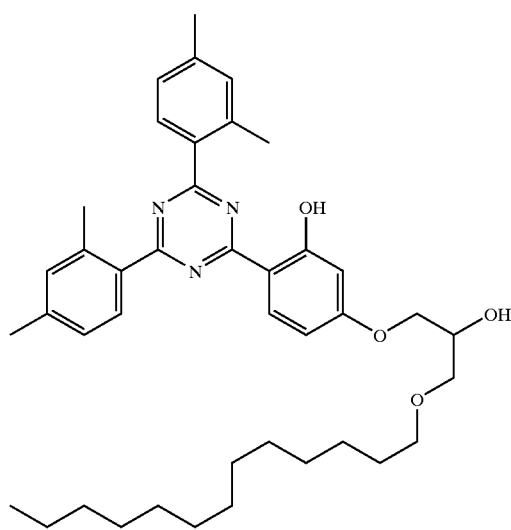
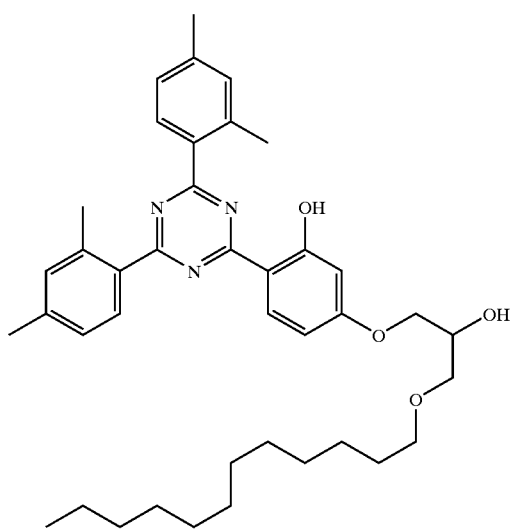

TABLE D-continued

Stabilisers which can be added, for example, to the mixtures according to the invention are mentioned below.

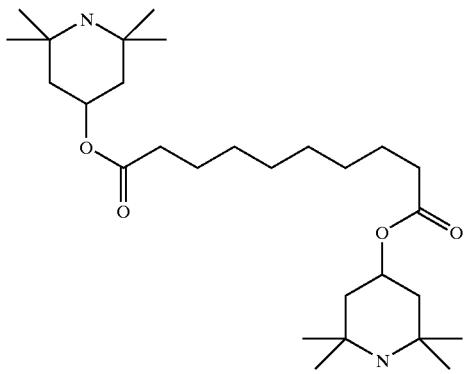 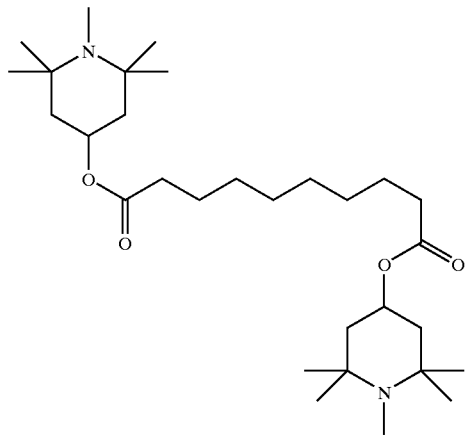

The following examples are intended to explain the invention without restricting it. Above and below, percentages are percent by weight. All temperatures are given in degrees Celsius. m.p. denotes melting point, cl.p. denotes clearing point. Furthermore, C=crystalline state, N=nematic phase, S=smectic phase and I=isotropic phase. The data between these symbols represent the transition temperatures. Δn denotes optical anisotropy (589 nm, 20° C.), the flow viscosity (mm²/sec) was determined at 20° C. The rotational viscosity γ₁ [mPa·s] was likewise determined at 20° C.

"Conventional work-up" means that water is added if necessary, the mixture is extracted with dichoromethane, diethyl ether, methyl tert-butyl ether or toluene, the phases are separated, the organic phase is dried and evaporated, and the product is purified by distillation under reduced pressure or crystallisation and/or chromatography. The following abbreviations are used:

| | |
|---|---|
| n-BuLi | 1.6 molar solution of n-butyllithium in n-hexane |
| DMAP | 4-(dimethylamino)pyridine |
| THF | tetrahydrofuran |
| DCC | N,N'-dicyclohexylcarbodiimide |
| LDA | lithium dimethylamide |

Example 1

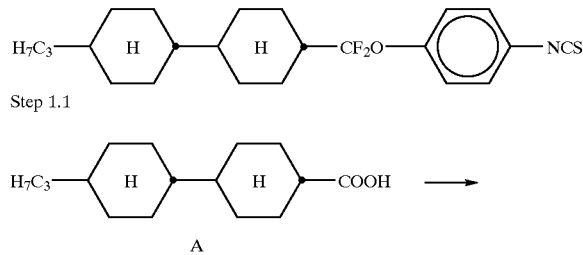

-continued

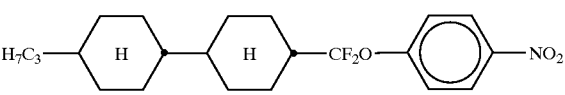

1.16 mol of 1,3-propanedithiol are added to a suspension consisting of 0.89 mol of A in 250 ml of toluene and 250 ml of isooctane. The suspension is heated to 50° C., and 1.16 mol of trifluoromethanesulfonic acid are added. The reaction mixture is heated to 102–104° C. while the water formed is removed azeotropically. After methyl tert-butyl ether has been added at 90° C., the reaction solution is cooled to 0° C. and filtered under N₂. The crystals are washed with tert-butyl ether and dried under reduced pressure.

Step 1.2

A mixture of 80 mmol of 4-nitrophenol, 100 ml of dichloromethane and 95 mmol of triethylamine is added slowly at −70° C. to a solution of 50 mmol of B in 250 ml of dichloromethane. After 5 minutes, 270 mmol of triethylamine trishydrofluoride are added, and, after a further 5 minutes, a suspension of 270 mmol of dibromodimethylhydantoin (DBH) in 150 ml of dichloromethane is added. The mixture is stirred at −70° C. for 1 hour, then allowed to warm to −20° C. and poured into 2.5 l of ice-cold 1N NaOH solution. The mixture is adjusted to pH 9–10, and the organic phase is extracted, washed with NaHCO₃ solution and water, dried over MgSO₄ and evaporated to dryness. The crude product is chromatographed over silica gel in heptane/MTB ether 9:1 and recrystallised from heptane.

Step 1.3

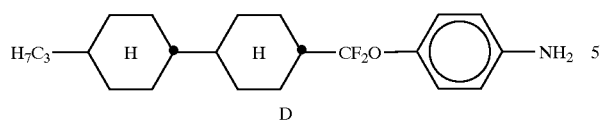

D

A solution of 100 mmol of C in 600 ml of THF is hydrogenated in the presence of 5 g of Pd/carbon until the take-up of hydrogen is complete. The catalyst is filtered off, and the filtrate is evaporated to dryness.

Step 1.4

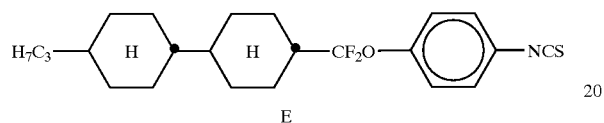

E

A solution of 50 mmol of D and 120 mmol of thiocarbonylbisimidazole in 400 ml of dichloromethane is stirred at room temperature for 24 hours. The reaction solution is filtered and evaporated to dryness, and the residue is chromatographed over silica gel using heptane/MTB ether 9:1. The product is recrystallised from heptane. C 43 N 223.8 I, $\Delta\epsilon=10.9$, $\Delta n=0.1781$ The following compounds of the formula

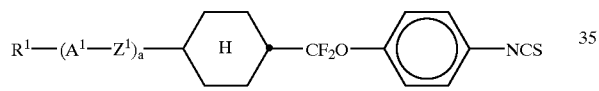

are prepared analogously:

| $R^1$ | $—(A^1—Z^1)_a—$ |
|---|---|
| $CH_3$ | — |
| $C_2H_5$ | — |
| $n-C_4H_9$ | — |
| $n-C_5H_{11}$ | — |
| $n-C_6H_{13}$ | — |
| $n-C_7H_{15}$ | — |
| $CH_3O$ | — |
| $C_2H_5O$ | — |
| $n-C_3H_7O$ | — |
| $n-C_4H_9O$ | — |
| $n-C_5H_{11}O$ | — |
| $n-C_6H_{13}O$ | — |
| $n-C_7H_{15}O$ | — |
| $CH_2=CH$ | — |
| $CH_3CH_2=CH$ | — |
| $CH_2=CHC_2H_4$ | — |
| $CH_3CH=CHC_2H_4$ | — |
| $CH_3$ | —⬡H— |
| $C_2H_5$ | —⬡H— |
| $n-C_3H_7$ | —⬡H— |
| $n-C_4H_9$ | —⬡H— |
| $n-C_5H_{11}$ | —⬡H— |
| $n-C_6H_{13}$ | —⬡H— |
| $n-C_7H_{15}$ | —⬡H— |
| $CH_3O$ | —⬡H— |
| $C_2H_5O$ | —⬡H— |
| $n-C_3H_7O$ | —⬡H— |
| $n-C_4H_9O$ | —⬡H— |
| $n-C_5H_{11}O$ | —⬡H— |
| $n-C_6H_{13}O$ | —⬡H— |
| $n-C_7H_{15}O$ | —⬡H— |
| $CH_2=CH$ | —⬡H— |
| $CH_3CH_2=CH$ | —⬡H— |
| $CH_2=CHC_2H_4$ | —⬡H— |

-continued

| R¹ | —(A¹—Z¹)ₐ— |
|---|---|
| CH₃CH=CHC₂H₄ | cyclohexyl (H) |
| CH₃ | 1,3-dioxane |
| C₂H₅ | 1,3-dioxane |
| n-C₃H₇ | 1,3-dioxane |
| n-C₄H₉ | 1,3-dioxane |
| n-C₅H₁₁ | 1,3-dioxane |
| n-C₆H₁₃ | 1,3-dioxane |
| n-C₇H₁₅ | 1,3-dioxane |
| CH₃O | 1,3-dioxane |
| C₂H₅O | 1,3-dioxane |
| n-C₃H₇O | 1,3-dioxane |
| n-C₄H₉O | 1,3-dioxane |
| n-C₅H₁₁O | 1,3-dioxane |
| n-C₆H₁₃O | 1,3-dioxane |

-continued

| R¹ | —(A¹—Z¹)ₐ— |
|---|---|
| n-C₇H₁₅O | 1,3-dioxane |
| CH₂=CH | 1,3-dioxane |
| CH₃CH₂=CH | 1,3-dioxane |
| CH₂=CHC₂H₄ | 1,3-dioxane |
| CH₃CH=CHC₂H₄ | 1,3-dioxane |
| CH₃ | cyclohexyl-CH₂CH₂— |
| C₂H₅ | cyclohexyl-CH₂CH₂— |
| n-C₃H₇ | cyclohexyl-CH₂CH₂— |
| n-C₄H₉ | cyclohexyl-CH₂CH₂— |
| n-C₅H₁₁ | cyclohexyl-CH₂CH₂— |
| n-C₆H₁₃ | cyclohexyl-CH₂CH₂— |
| n-C₇H₁₅ | cyclohexyl-CH₂CH₂— |
| CH₃O | cyclohexyl-CH₂CH₂— |
| C₂H₅O | cyclohexyl-CH₂CH₂— |
| n-C₃H₇O | cyclohexyl-CH₂CH₂— |

-continued

| R¹ | —(A¹—Z¹)ₐ— |
|---|---|
| n-C₄H₉O | 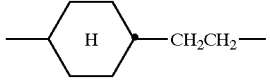 |
| N-C₅H₁₁O | 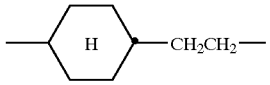 |
| n-C₆H₁₃O | 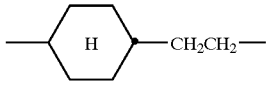 |
| n-C₇H₁₅O | 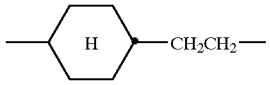 |
| CH₂=CH | 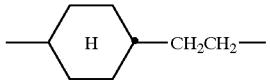 |
| CH₃CH₂=CH | 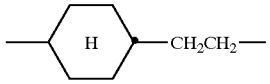 |
| CH₂=CHC₂H₄ | 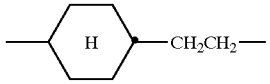 |
| CH₃CH=CHC₂H₄ | 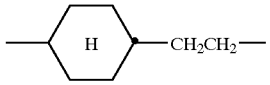 |

Example 2

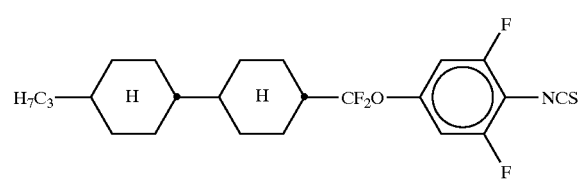

Step 2.1

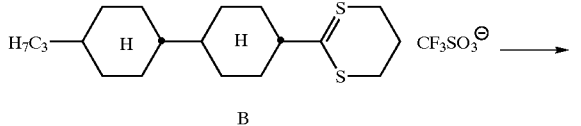
B

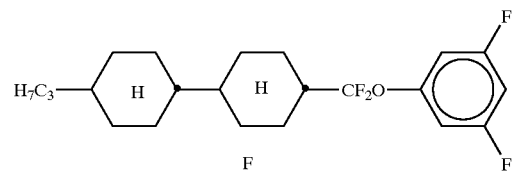
F

A mixture of 80 mmol of 3,5-difluorophenol, 100 ml of dichloromethane and 95 mmol of triethylamine is added slowly at –70° C. to a solution of 50 mmol of B in 250 ml of dichloromethane. After 5 minutes, 270 mmol of triethylamine trishydrofluoride are added, and, after a further 5 minutes, a suspension of 270 mmol of dibromodimethylhydantoin (DBH) in 150 ml of dichloromethane is added. The mixture is stirred at –70° C. for 1 hour, then allowed to warm to –20° C. and poured into 2.5 l of ice-cold 1N NaOH solution. The organic phase is subjected to conventional work-up. The crude product is chromatographed over a silica gel frit in heptane and recrystallised from heptane.

Step 2.2

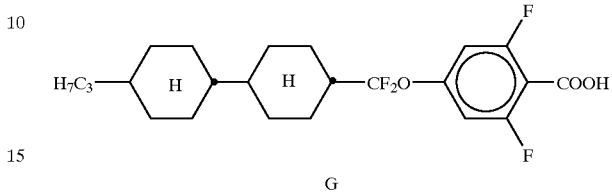
G 80 mmol of n-BuLi (15% in hexane) are added dropwise at –70° C. to a solution of 80 mmol of F in 400 ml of THF. The mixture is stirred at –70° C. for 3 hours, and an excess of dry $CO_2$ is then passed in. The mixture is allowed to warm to room temperature and is poured onto 700 g of ice. The mixture is rendered alkaline by addition of 1 N NaOH, and the organic phase is separated off and discarded. The aqueous solution is acidified using conc. HCl, and the precipitated product is filtered off with suction and washed with cold water. The product is crystallised from glacial acetic acid.

Step 2.3

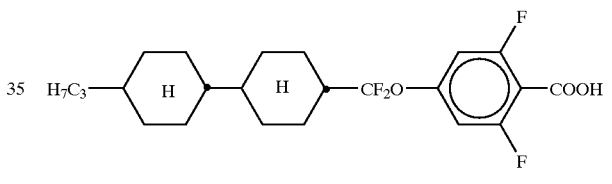
H

A solution of 50 mmol of G and 70 mmol of diphenoxyphosphoryl azide (DPPA) in 300 ml of dry t-Butanol is heated at the boil for 18 hours. 300 ml of ice-cold saturated $NaHCO_3$ solution and 200 ml of dichloromethane are added, and the organic phase is separated off and evaporated to dryness in a rotary evaporator. The crude t-butylurethane formed as an intermediate is taken up in 100 ml of trifluoroacetic acid and stirred at room temperature for 2 hours. The reaction solution is evaporated to dryness in a rotary evaporator, chromatographed over silica gel in heptane/MTB ether 9:1 and crystallised from heptane.

Step 2.4

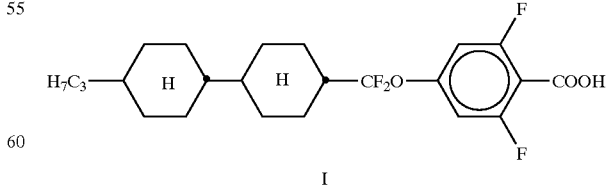
I

A solution of 30 mmol of H and 40 mmol of thiocarbonylbisimidazole in 250 ml of dichloromethane is stirred at room temperature for 24 hours. The reaction solution is filtered and evaporated to dryness, and the residue is chromatographed over silica gel using heptane/MTB ether 9:1. The product is recrystallised from heptane.

The following compounds of the formula

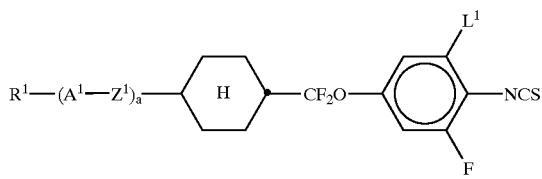

are prepared analogously:

| R$^1$ | —(A$^1$—Z$^1$)$_a$— | L$^1$ |
|---|---|---|
| CH$_3$ | cyclohexyl | H |
| CH$_3$ | cyclohexyl | F |
| C$_2$H$_5$ | cyclohexyl | H |
| C$_2$H$_5$ | cyclohexyl | F |
| n-C$_3$H$_7$ | cyclohexyl | H |
| n-C$_4$H$_9$ | cyclohexyl | H |
| n-C$_4$H$_9$ | cyclohexyl | F |
| n-C$_5$H$_{11}$ | cyclohexyl | H |
| n-C$_5$H$_{11}$ | cyclohexyl | F |
| n-C$_6$H$_{13}$ | cyclohexyl | H |
| n-C$_6$H$_{13}$ | cyclohexyl | F |
| n-C$_7$H$_{15}$ | cyclohexyl | H |
| n-C$_7$H$_{15}$ | cyclohexyl | F |
| CH$_3$O | cyclohexyl | H |
| CH$_3$O | cyclohexyl | F |
| C$_2$H$_5$O | cyclohexyl | H |
| C$_2$H$_5$O | cyclohexyl | F |
| n-C$_3$H$_7$O | cyclohexyl | H |
| n-C$_3$H$_7$O | cyclohexyl | F |
| n-C$_4$H$_9$O | cyclohexyl | H |
| n-C$_4$H$_9$O | cyclohexyl | F |
| n-C$_5$H$_{11}$O | cyclohexyl | H |
| n-C$_5$H$_{11}$O | cyclohexyl | F |
| n-C$_6$H$_{13}$O | cyclohexyl | H |
| n-C$_6$H$_{13}$O | cyclohexyl | F |
| n-C$_7$H$_{15}$O | cyclohexyl | H |
| n-C$_7$H$_{15}$O | cyclohexyl | F |

-continued

| R¹ | —(A¹—Z¹)ₐ— | L¹ |
|---|---|---|
| CH₂=CH | cyclohexyl (H) | H |
| CH₂=CH | cyclohexyl (H) | F |
| CH₃CH₂=CH | cyclohexyl (H) | H |
| CH₃CH₂=CH | cyclohexyl (H) | F |
| CH₂=CHC₂H₄ | cyclohexyl (H) | H |
| CH₂=CHC₂H₄ | cyclohexyl (H) | F |
| CH₃CH=CHC₂H₄ | cyclohexyl (H) | H |
| CH₃CH=CHC₂H₄ | cyclohexyl (H) | F |
| CH₃ | — | H |
| CH₃ | — | F |
| C₂H₅ | — | H |
| C₂H₅ | — | F |
| n-C₃H₇ | — | H |
| n-C₃H₇ | — | F |
| n-C₄H₉ | — | H |
| n-C₄H₉ | — | F |
| n-C₅H₁₁ | — | H |
| n-C₅H₁₁ | — | F |
| n-C₆H₁₃ | — | H |
| n-C₆H₁₃ | — | F |
| n-C₇H₁₅ | — | H |
| n-C₇H₁₅ | — | F |
| CH₃O | — | H |
| CH₃O | — | F |
| C₂H₅O | — | H |
| C₂H₅O | — | F |
| n-C₃H₇O | — | H |
| n-C₃H₇O | — | F |
| n-C₄H₉O | — | H |
| n-C₄H₉O | — | F |
| n-C₅H₁₁O | — | H |
| n-C₅H₁₁O | — | F |
| n-C₆H₁₃O | — | H |
| n-C₆H₁₃O | — | F |
| n-C₇H₁₅O | — | H |
| n-C₇H₁₅O | — | F |
| CH₂=CH | — | H |
| CH₂=CH | — | F |
| CH₃CH₂=CH | — | H |
| CH₃CH₂=CH | — | F |
| CH₂=CHC₂H₄ | — | H |
| CH₂=CHC₂H₄ | — | F |
| CH₃CH=CHC₂H₄ | — | H |
| CH₃CH=CHC₂H₄ | — | F |

-continued

| R¹ | —(A¹—Z¹)ₐ— | L¹ |
|---|---|---|
| CH₃ | 1,3-dioxane | H |
| CH₃ | 1,3-dioxane | F |
| C₂H₅ | 1,3-dioxane | H |
| C₂H₅ | 1,3-dioxane | F |
| n-C₃H₇ | 1,3-dioxane | H |
| n-C₃H₇ | 1,3-dioxane | F |
| n-C₄H₉ | 1,3-dioxane | H |
| n-C₄H₉ | 1,3-dioxane | F |
| n-C₅H₁₁ | 1,3-dioxane | H |
| n-C₅H₁₁ | 1,3-dioxane | F |
| n-C₆H₁₃ | 1,3-dioxane | H |
| n-C₆H₁₃ | 1,3-dioxane | F |
| n-C₇H₁₅ | 1,3-dioxane | H |
| n-C₇H₁₅ | 1,3-dioxane | F |

-continued

| R¹ | —(A¹—Z¹)ₐ— | L¹ |
|---|---|---|
| CH₃O | dioxane | H |
| CH₃O | dioxane | F |
| C₂H₅O | dioxane | H |
| C₂H₅O | dioxane | F |
| n-C₃H₇O | dioxane | H |
| n-C₃H₇O | dioxane | F |
| n-C₄H₉O | dioxane | H |
| n-C₄H₉O | dioxane | F |
| n-C₅H₁₁O | dioxane | H |
| n-C₅H₁₁O | dioxane | F |
| n-C₆H₁₃O | dioxane | H |
| n-C₆H₁₃O | dioxane | F |
| n-C₇H₁₅O | dioxane | H |

-continued

| R¹ | —(A¹—Z¹)ₐ— | L¹ |
|---|---|---|
| n-C₇H₁₅O | dioxane | F |
| CH₂=CH | dioxane | H |
| CH₂=CH | dioxane | F |
| CH₃CH₂=CH | dioxane | H |
| CH₃CH₂=CH | dioxane | F |
| CH₂=CHC₂H₄ | dioxane | H |
| CH₂=CHC₂H₄ | dioxane | F |
| CH₃CH=CHC₂H₄ | dioxane | H |
| CH₃CH=CHC₂H₄ | dioxane | F |
| CH₃ | cyclohexyl-CH₂CH₂— | H |
| CH₃ | cyclohexyl-CH₂CH₂— | F |
| C₂H₅ | cyclohexyl-CH₂CH₂— | H |
| C₂H₅ | cyclohexyl-CH₂CH₂— | F |
| n-C₃H₇ | cyclohexyl-CH₂CH₂— | H |

-continued
| R¹ | —(A¹—Z¹)ₐ— | L¹ |
|---|---|---|
| n-C₃H₇ | 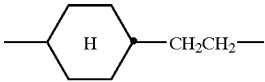 | F |
| n-C₄H₉ | 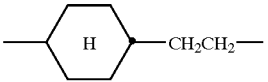 | H |
| n-C₄H₉ | 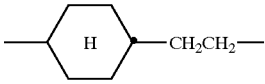 | F |
| n-C₅H₁₁ | 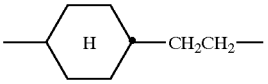 | H |
| n-C₅H₁₁ | 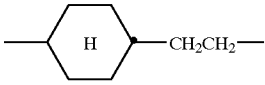 | F |
| n-C₆H₁₃ | 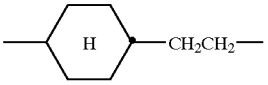 | H |
| n-C₆H₁₃ | 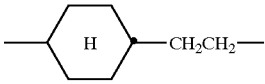 | F |
| n-C₇H₁₅ | 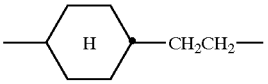 | H |
| n-C₇H₁₅ | 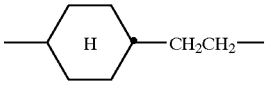 | F |
| CH₃O | 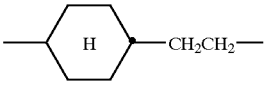 | H |
| CH₃O | 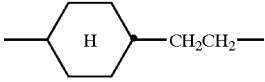 | F |
| C₂H₅O | 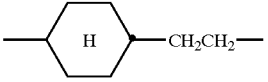 | H |
| C₂H₅O | 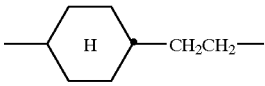 | F |
| n-C₃H₇O | 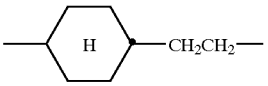 | H |
| n-C₃H₇O | 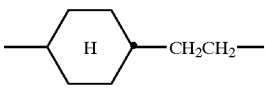 | F |
-continued
| R¹ | —(A¹—Z¹)ₐ— | L¹ |
|---|---|---|
| n-C₄H₉O | 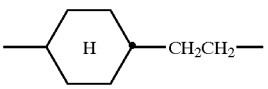 | H |
| n-C₄H₉O | 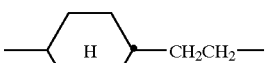 | F |
| n-C₅H₁₁O | 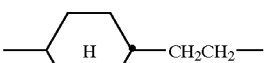 | H |
| n-C₅H₁₁O | 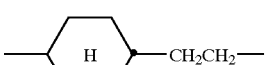 | F |
| n-C₆H₁₃O | 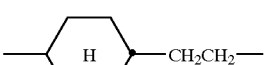 | H |
| n-C₆H₁₃O | 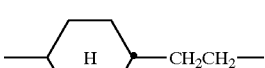 | F |
| n-C₇H₁₅O | 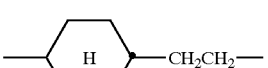 | H |
| n-C₇H₁₅O | 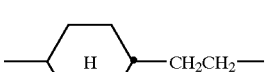 | F |
| CH₂=CH | 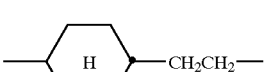 | H |
| CH₂=CH | 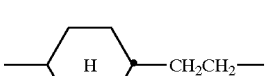 | F |
| CH₃CH₂=CH | 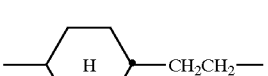 | H |
| CH₃CH₂=CH | 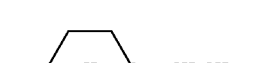 | F |
| CH₂=CHC₂H₄ | 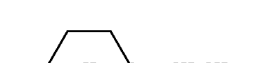 | H |
| CH₂=CHC₂H₄ | 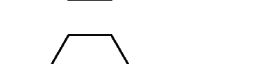 | F |
| CH₃CH=CHC₂H₄ | 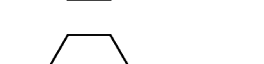 | H |

-continued

| R$^1$ | —(A$^1$—Z$^1$)$_a$— | L$^1$ |
|---|---|---|
| CH$_3$CH=CHC$_2$H$_4$ | 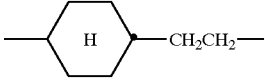 | F |

Mixture Examples

Example A

| | | | |
|---|---|---|---|
| BCH-3F.F | 10.80% | Clearing point [° C.]: | 103.3 |
| BCH-5F.F | 9.00% | Δn [589 nm, 20° C.]: | 0.1051 |
| ECCP-30CF$_3$ | 4.50% | Δε [1 kHz, 20° C.]: | 5.9 |
| ECCP-50CF$_3$ | 4.50% | | |
| CBC-33F | 1.80% | | |
| CBC-53F | 1.80% | | |
| CBC-55F | 1.80% | | |
| PCH-6F | 7.20% | | |
| PCH-7F | 5.40% | | |
| CCP-20CF$_3$ | 7.20% | | |
| CCP-30CF$_3$ | 10.80% | | |
| CCP-40CF$_3$ | 6.30% | | |
| CCP-50CF$_3$ | 9.90% | | |
| PCH-5F | 9.00% | | |
| CCQP-3-S | 10.00% | | |

Example B

| | | | |
|---|---|---|---|
| BCH-3F.F | 10.80% | Clearing point [° C.]: | 99.7 |
| BCH-5F.F | 9.00% | Δn [589 nm, 20° C.]: | 0.1039 |
| ECCP-30CF$_3$ | 4.50% | Δε [1 kHz, 20° C.]: | 6.3 |
| ECCP-50CF$_3$ | 4.50% | γ$_1$ [20° C.] | 151 |
| CBC-33F | 1.80% | | |
| CBC-53F | 1.80% | | |
| CBC-55F | 1.80% | | |
| PCH-6F | 7.20% | | |
| PCH-7F | 5.40% | | |
| CCP-20CF$_3$ | 7.20% | | |
| CCP-30CF$_3$ | 10.80% | | |
| CCP-40CF$_3$ | 6.30% | | |
| CCP-50CF$_3$ | 9.90% | | |
| PCH-5F | 9.00% | | |
| CCQU-3-S | 10.00% | | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A liquid-crystalline compound of the formula I

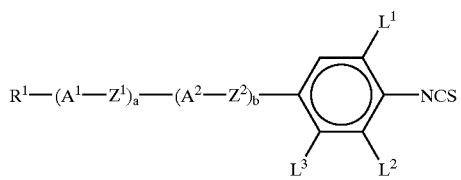

I in which

R$^1$ is an alkyl radical having from 1 to 15 carbon atoms which is unsubstituted, monosubstituted by CN or CF$_3$ or mono-to per halo-substituted by halogen, where one or more CH$_2$ groups in these radicals are optionally replaced by —O—, —S—, —CH=CH—, —C≡C—, —OC—O— or —O—CO— in such a way that O atoms are not linked directly to one another, A$^1$ and A$^2$ are each, independently of one another,
 a) a 1,4-cyclohexenylene or 1,4-cyclohexylene radical, in which one or two non-adjacent CH$_2$ groups are optionally replaced by —O— or —S—,
 b) a 1,4-phenylene radical, in which one or two CH groups are optionally replaced by N,
 c) a radical selected from the group consisting of piperidine-1,4-diyl, 1,4-bicyclo[2.2.2]octylene, phenanthrene-2,7-diyl, naphthalene-2,6-diyl, decahydronaphthalene-2,6-diyl and 1,2,3,4-tetrahydronaphthalene-2,6-diyl,
 where the radicals a), b) and c) are optionally mono-substituted or polysubstituted by halogen atoms, Z$^1$ and Z$^2$ are each, independently of one another, —CO—O—, —O—CO—, —CF$_2$O—, —OCF$_2$—, —CH$_2$O—, —OCH$_2$—, —CH$_2$CH$_2$—, —(CH$_2$)$_4$—, —C$_2$F$_4$—, —CH$_2$CF$_2$—, —CF$_2$CH$_2$—, —CF=CF—, —CH=CH—, —C≡C— or a single bond, with the proviso that at least one of Z$^1$ and Z$^2$ is —CF$_2$O— or —OCF$_2$—, a is 0, 1 or 2, b is 1 or 2, and L$^1$, L$^2$ and L$^3$ are each, independently of one another, H, F or Cl.

2. A liquid-crystalline compound according to claim 1, wherein R$^1$ is a straight-chain alkyl radical having from 1 to 10 carbon atoms or an alkenyl radical having from 2 to 10 carbon atoms.

3. A liquid-crystalline compound according to claim 1, wherein a+b=1 or 2.

4. A liquid-crystalline compound according to claim 2, wherein a+b=1 or 2.

5. A liquid-crystalline compound according to claim 1, wherein L$^1$ is fluorine and L$^2$ is fluorine or hydrogen.

6. A liquid-crystalline compound according to claim 2, wherein L$^1$ is fluorine and L$^2$ is fluorine or hydrogen.

7. A liquid-crystalline compound according to claim 3, wherein L$^1$ is fluorine and L$^2$ is fluorine or hydrogen.

8. A liquid-crystalline compound according to claim 5, wherein L$^2$ and L$^3$ are fluorine.

9. A liquid-crystalline compound of claim 1, which is of one of the formulae I1 to I94:

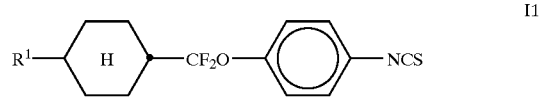

I1

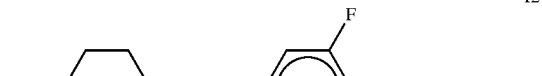

I2

I3

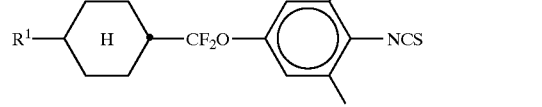

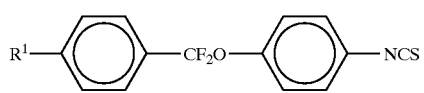
I4
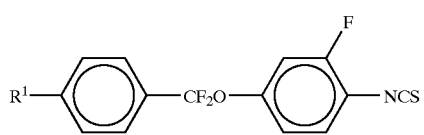
I5
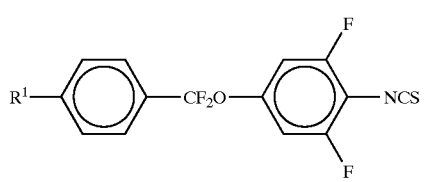
I6
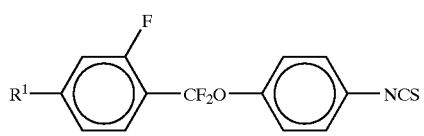
I7
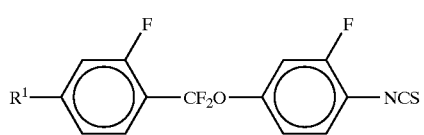
I8
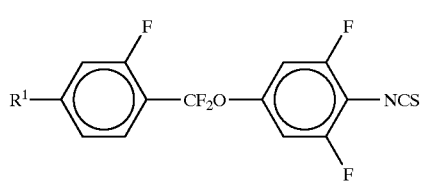
I9
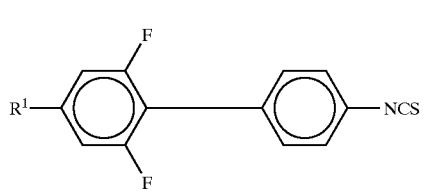
I10
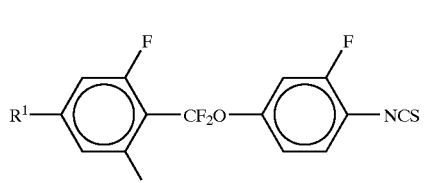
I11
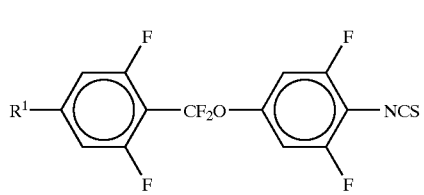
I12
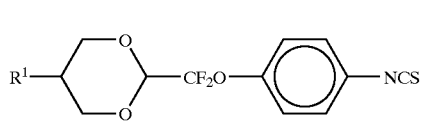
I13
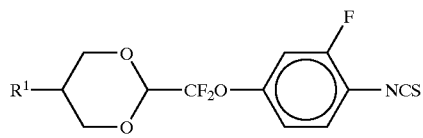
I14
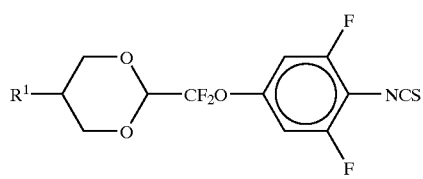
I15
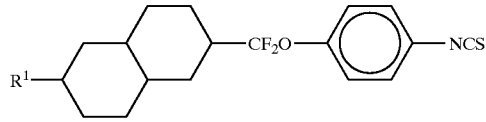
I16
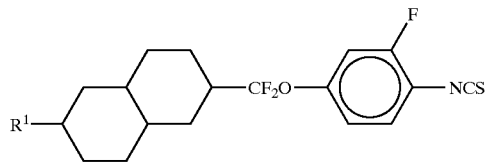
I17
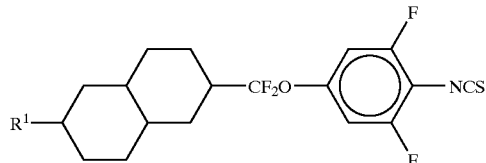
I18
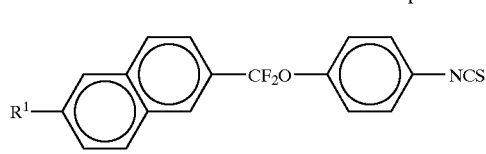
I19
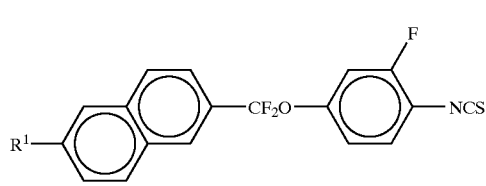
I20
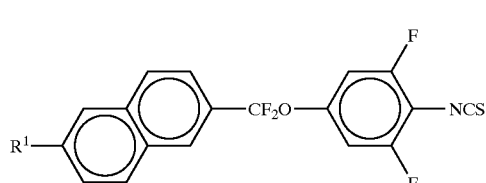
I21
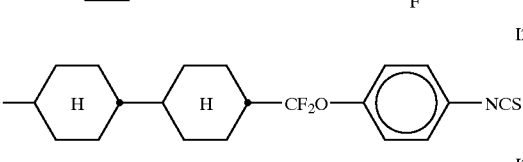
I22
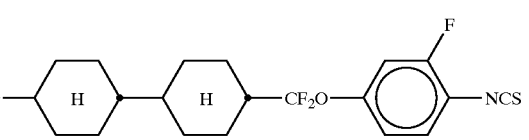
I23

I24 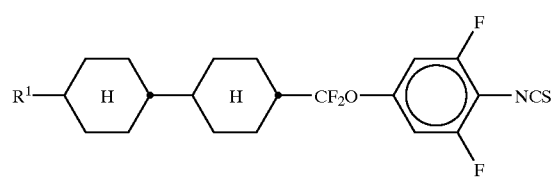
I25 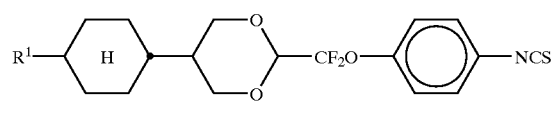
I26 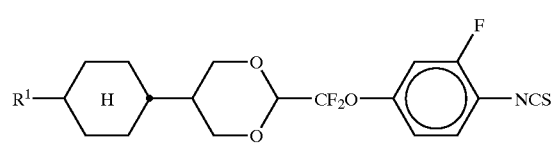
I27 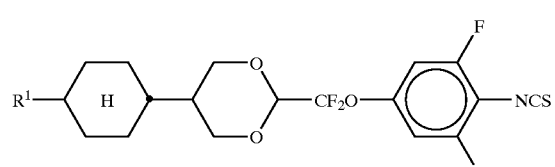
I28 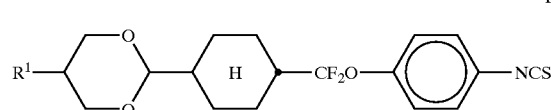
I29 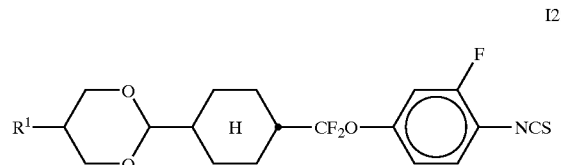
I30 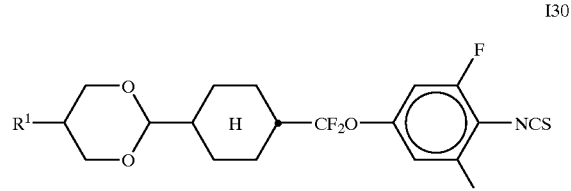
I31 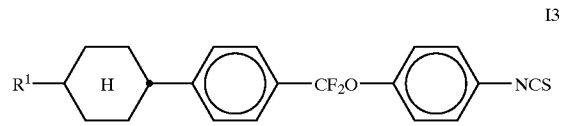
I32 
I33 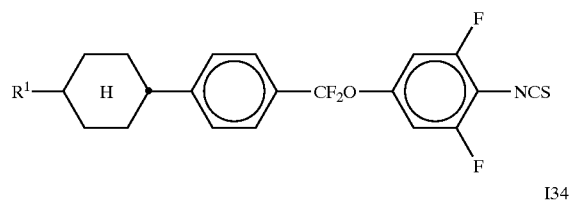
I34 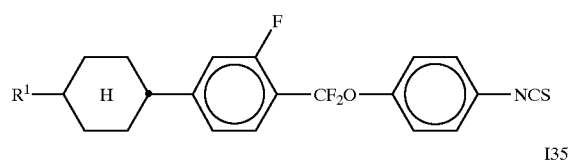
I35 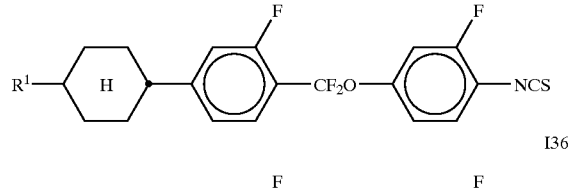
I36 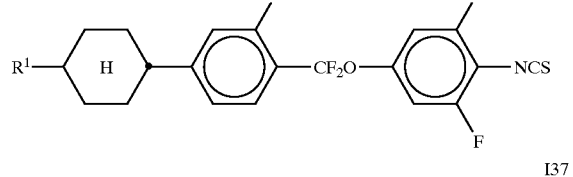
I37 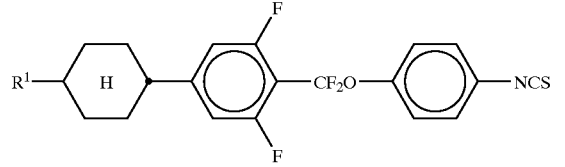
I38 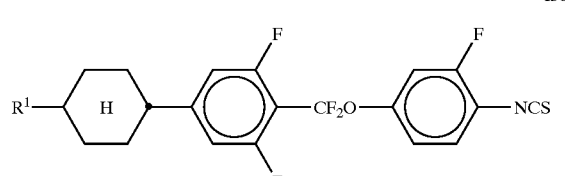
I39 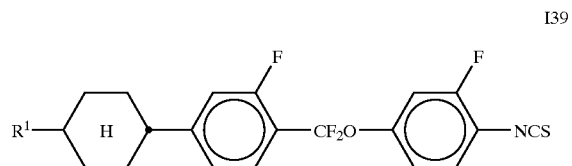
I40 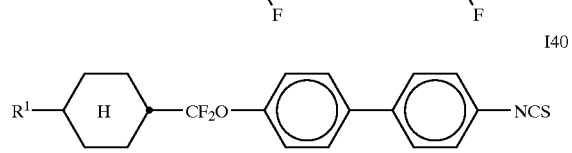
I41 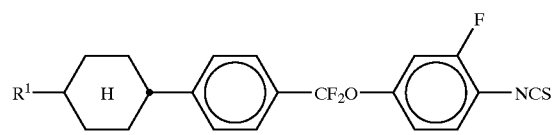

I42 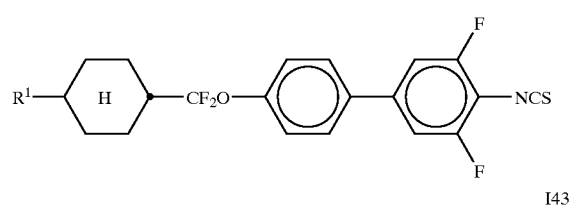
I51 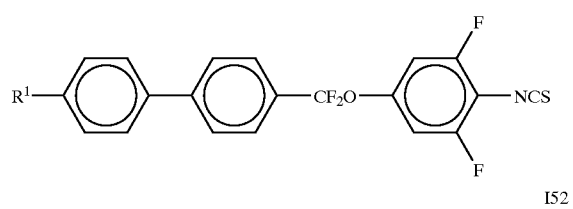
I43 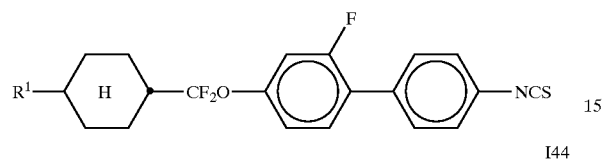
I52 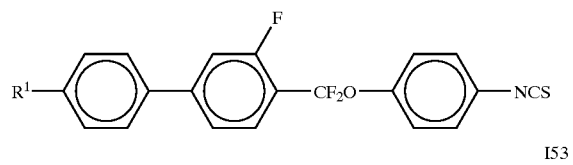
I44 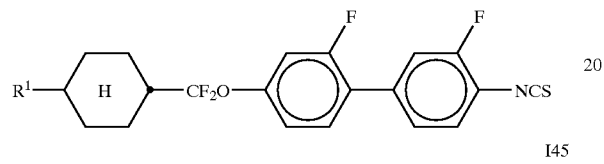
I53 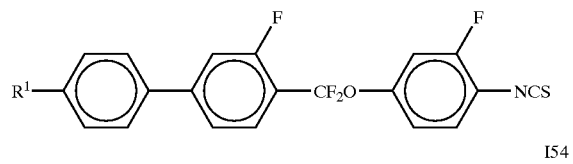
I45 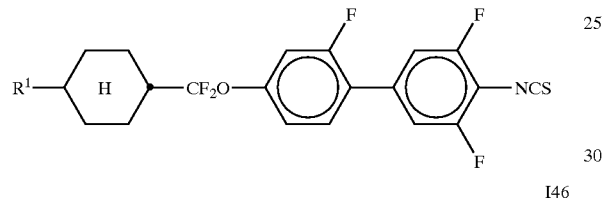
I54 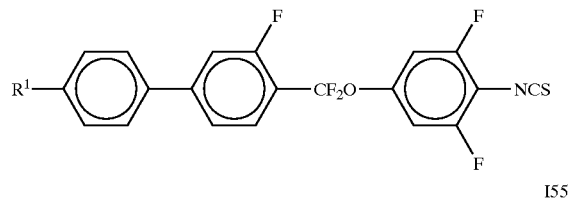
I46 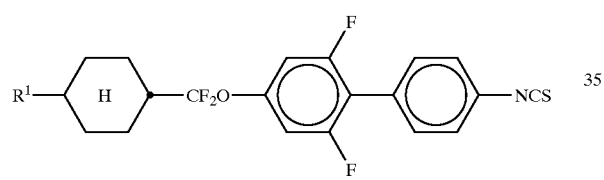
I55 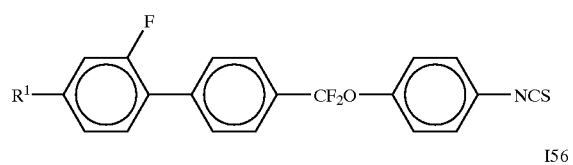
I47 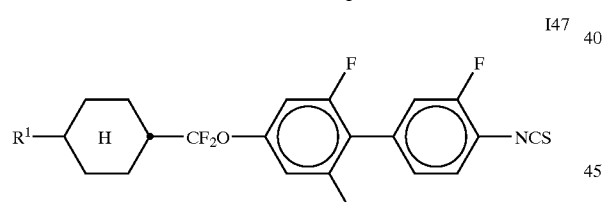
I56 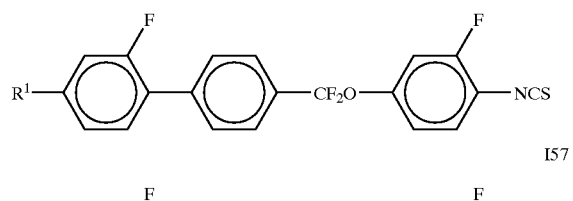
I48 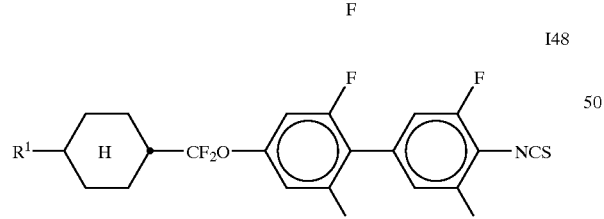
I57 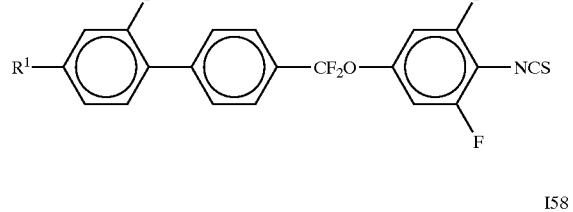
I49 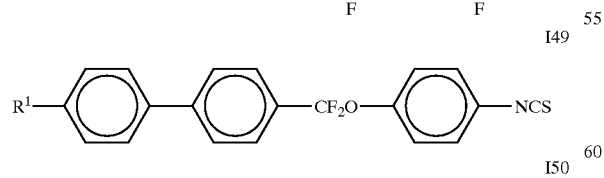
I58 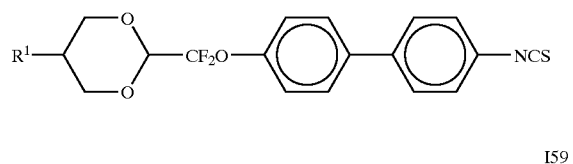
I50 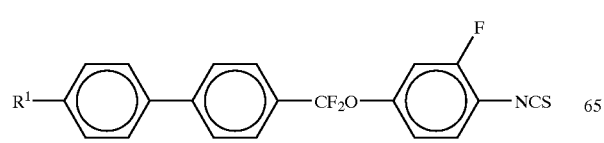
I59 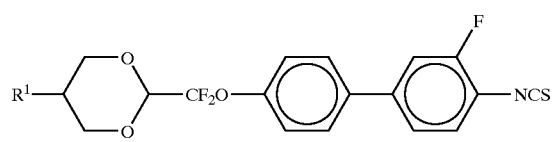

I60
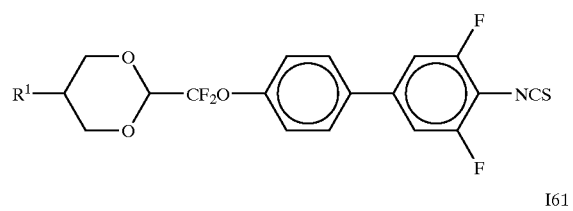
I61
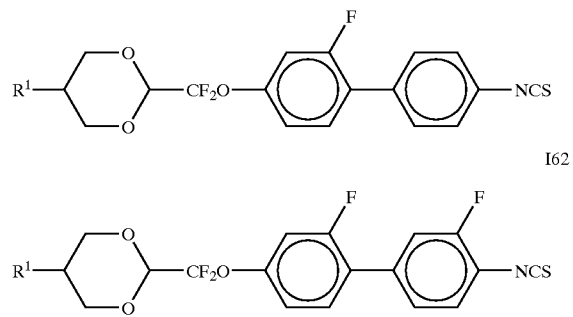
I62
I63
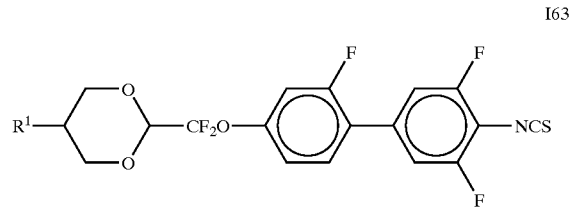
I64
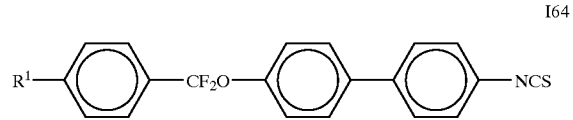
I65
I66
I67
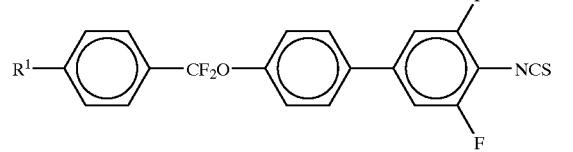
I68
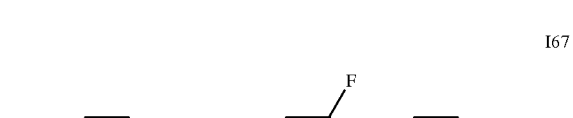
I69
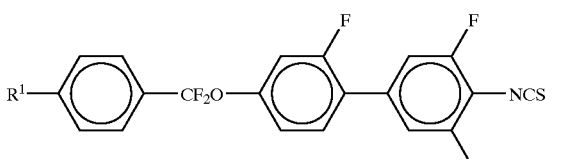
I70
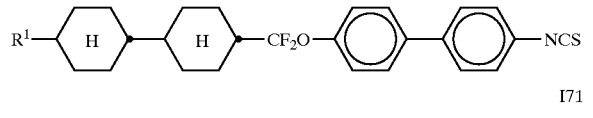
I71
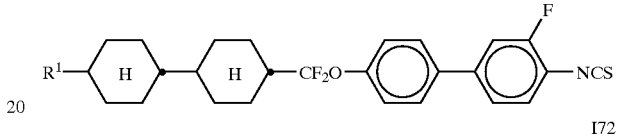
I72
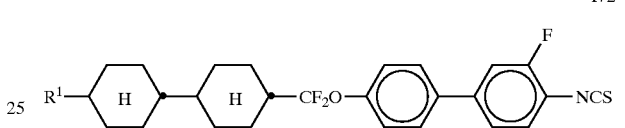
I73
I74
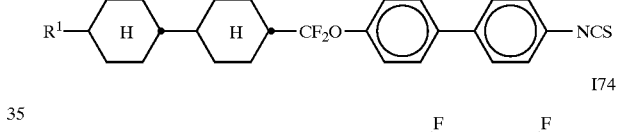
I75
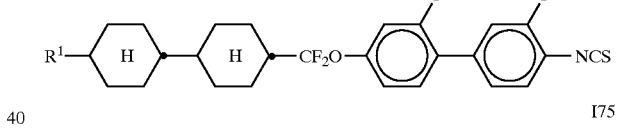
I76
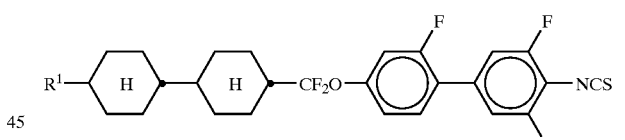
I77
I78
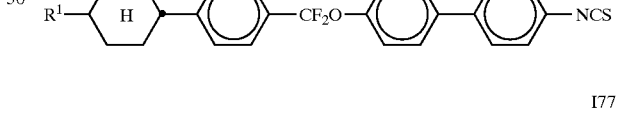

in which

R¹ is as defined in claim 1 and (F) is fluoro or hydrogen.

10. A liquid-crystalline medium comprising at least two mesogenic compounds, wherein at least one compound is of the formula I according to claim 1.

11. An electro-optical liquid-crystal display containing a liquid-crystalline, medium according to claim 10.

12. A compound of claim 1, wherein a=o.

13. A compound of claim 1, wherein one of $Z^1$ and $Z^2$ is —CF₂O— or —OCF₂— and the other is a single bond.

14. A liquid-crystalline medium of claim 10, which exhibits a nematic phase range from −20° C. to above 100° C., a dielectric anisotropy, Δε, ≧4.

15. A liquid-crystalline medium of claim 10, wherein the proportion of compounds of the formula I is from 5–95% by weight.

16. A compound of claim 1, wherein R¹ is ethyl or propyl.

* * * * *